(12) United States Patent
Thuresson et al.

(10) Patent No.: US 8,236,292 B2
(45) Date of Patent: Aug. 7, 2012

(54) LIQUID DEPOT FORMULATIONS

(75) Inventors: Krister Thuresson, Lund (SE); Fredrik Tiberg, Lund (SE); Markus Johansson, Lund (SE); Ian Harwigsson, Lund (SE); Fredrik Joabsson, Lund (SE); Markus Johnsson, Lund (SE)

(73) Assignee: Camurus AB, Lund (SE)

( * ) Notice: Subject to any disclaimer, the term of this patent is extended or adjusted under 35 U.S.C. 154(b) by 583 days.

(21) Appl. No.: 11/628,007

(22) PCT Filed: Jun. 6, 2005

(86) PCT No.: PCT/GB2005/002217
§ 371 (c)(1),
(2), (4) Date: Jul. 24, 2007

(87) PCT Pub. No.: WO2005/117830
PCT Pub. Date: Dec. 15, 2005

(65) Prior Publication Data
US 2008/0085263 A1    Apr. 10, 2008

(30) Foreign Application Priority Data

Jun. 4, 2004 (GB) ................................. 0412530.8
Jan. 14, 2005 (GB) ................................. 0500807.3
Apr. 18, 2005 (GB) ................................. 0507811.8

(51) Int. Cl.
*C07F 9/02* (2006.01)
*A61K 31/355* (2006.01)
*A61K 31/40* (2006.01)
*A61K 31/415* (2006.01)
*A61K 31/4164* (2006.01)
*A61K 31/445* (2006.01)
*A61K 31/55* (2006.01)
*A61K 31/66* (2006.01)
*A61P 31/00* (2006.01)
*C07D 311/04* (2006.01)

(52) U.S. Cl. ........ 424/85.7; 514/103; 514/221; 514/315; 514/397; 514/404; 514/419; 514/458; 514/558; 514/559; 514/560; 549/406; 554/80; 424/407

(58) Field of Classification Search ........................ None
See application file for complete search history.

(56) References Cited

U.S. PATENT DOCUMENTS
4,610,868 A * 9/1986 Fountain et al. ............. 424/1.21
(Continued)

FOREIGN PATENT DOCUMENTS
EP    0 767 656    7/2001
(Continued)

OTHER PUBLICATIONS

Shah et al, "Cubic phase gels as drug delivery systems", *Advanced Drug Delivery Reviews*, 2001, 47 (2-3), p. 229-250.

(Continued)

*Primary Examiner* — Ernst Arnold
*Assistant Examiner* — Hong Yu
(74) *Attorney, Agent, or Firm* — Nixon & Vanderhye P.C.

(57) ABSTRACT

The present invention relates to pre-formulations comprising low viscosity, non-liquid crystalline, mixtures of: a) at least one neutral diacyl lipid and/or at least one tocopherol; b) at least one phospholipid; c) at least one biocompatible, oxygen containing, low viscosity organic solvent; wherein at least one bioactive agent is dissolved or dispersed in the low viscosity mixture and wherein the pre-formulation forms, or is capable of forming, at least one liquid crystalline phase structure upon contact with an aqueous fluid. The preformulations are suitable for generating parenteral, non-parenteral and topical depot compositions for sustained release of active agents. The invention additionally relates to a method of delivery of an active agent comprising administration of a preformulation of the invention, a method of treatment comprising administration of a preformulation of the invention and the use of a preformulation of the invention in a method for the manufacture of a medicament.

24 Claims, 4 Drawing Sheets

Plasma concentrations in the rat model after subcutaneous administration of formulations F and G.

U.S. PATENT DOCUMENTS

| | | | |
|---|---|---|---|
| 4,938,763 | A | 7/1990 | Dunn et al. |
| 5,480,656 | A | 1/1996 | Okada et al. |
| 5,807,573 | A | 9/1998 | Ljusberg-Wahren et al. |
| 5,955,502 | A * | 9/1999 | Hansen et al. .............. 514/558 |
| 6,071,524 | A | 6/2000 | Ribier et al. |
| 6,113,943 | A | 9/2000 | Okada et al. |
| 6,464,987 | B1 * | 10/2002 | Fanara et al. ............. 424/400 |
| 6,599,517 | B1 | 7/2003 | Ljusberg-Wahren et al. |
| 6,630,115 | B1 | 10/2003 | Kaneeda et al. |
| 6,630,155 | B1 | 10/2003 | Chandrashekar et al. |
| 6,656,385 | B2 | 12/2003 | Lynch et al. |
| 6,660,278 | B1 | 12/2003 | Larsson et al. |
| 2002/0182247 | A1* | 12/2002 | Maruo et al. ............. 424/449 |
| 2003/0003144 | A1* | 1/2003 | Keller ...................... 424/456 |
| 2007/0265190 | A1* | 11/2007 | Thuresson et al. ............ 514/2 |
| 2008/0124394 | A1* | 5/2008 | Johnsson et al. ........... 424/484 |
| 2008/0146490 | A1* | 6/2008 | Joabsson et al. .............. 514/2 |
| 2009/0155193 | A1* | 6/2009 | Joabsson et al. ............ 424/59 |

FOREIGN PATENT DOCUMENTS

| | | |
|---|---|---|
| EP | 0767 656 B1 * | 7/2001 |
| WO | WO 95/34287 | 12/1995 |
| WO | 97/13528 A | 4/1997 |
| WO | WO 97/13528 A | 4/1997 |
| WO | 02/068562 | 9/2002 |
| WO | WO 02/068562 A | 9/2002 |
| WO | 2005/046642 A | 5/2005 |
| WO | WO 2005/046642 A | 5/2005 |

OTHER PUBLICATIONS

International Search Report of PCT/GB2005/002217, mailed Oct. 19, 2005.

Tiberg et al, "Drug Delivery Applications of Non-Lamellar Liquid Crystalline Phases and Nanoparticles", J.Drug Del. Sci. Tech., 21 (1) 101-109, 2011.

"Lipids: Structure, Physical Properties and Functionality", Larsson et al, The Oily Press; Copyright 2006, extract.

* cited by examiner

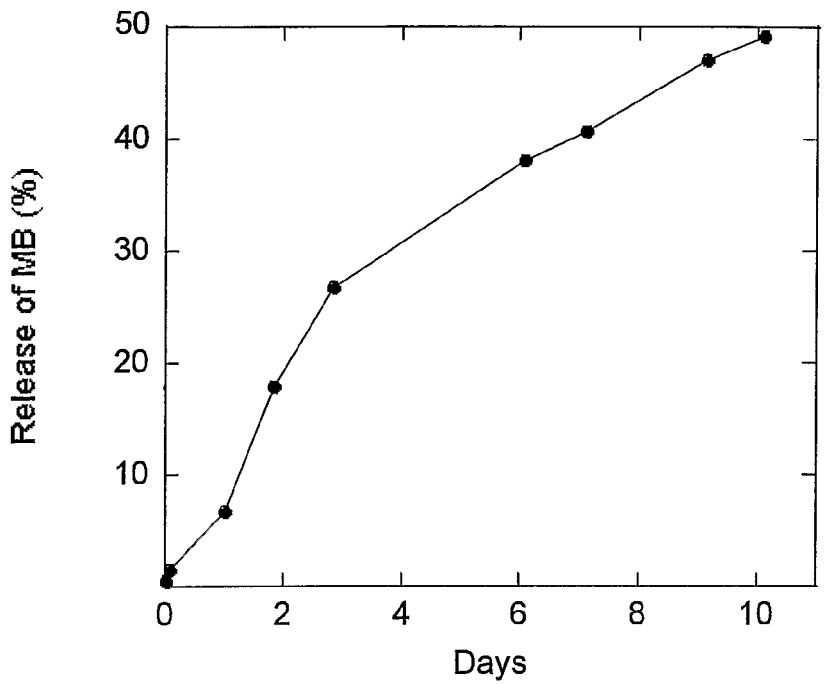
Figure 1. Cumulative release of MB from a depot forming a reversed hexagonal $H_{II}$ phase.
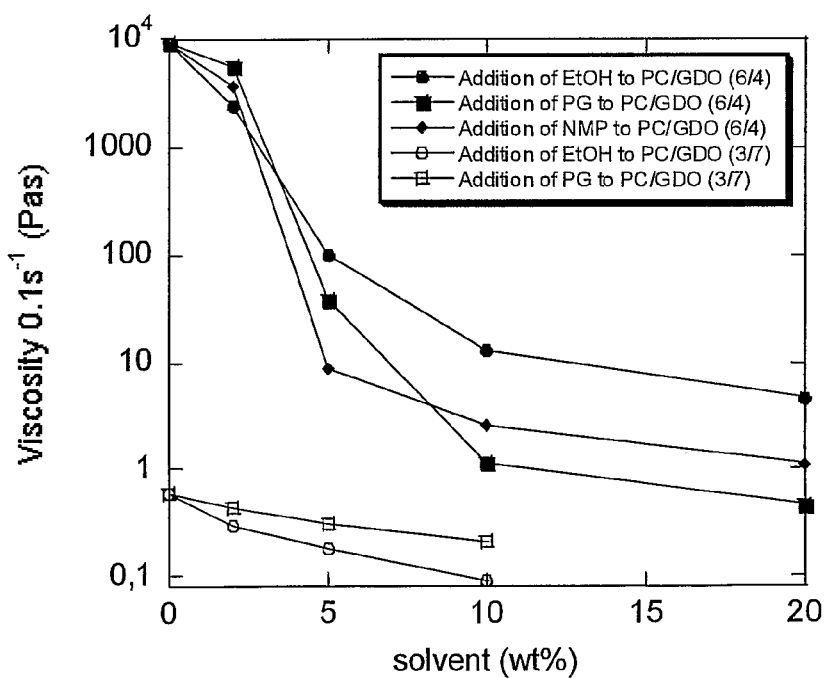
Figure 2. Decrease in viscosity of the depot precursor on addition of solvents. PC/GDO (6/4) is a precursor to a reversed hexagonal $H_{II}$ phase and PC/GDO (3/7) is a precursor to a reversed cubic $I_2$ phase.

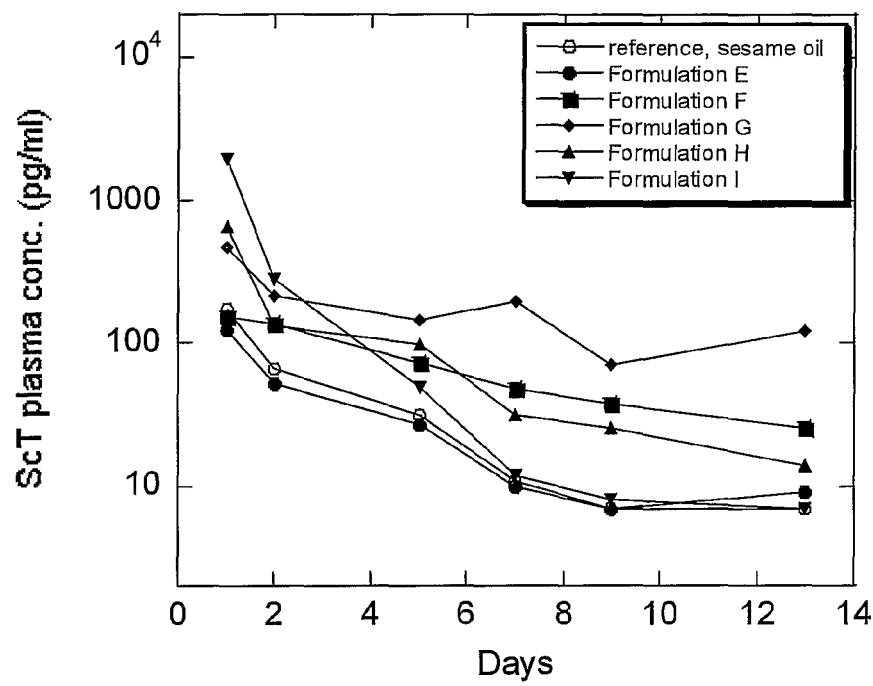
*Figure 3. Plasma concentrations in the rat model after subcutaneous administration of formulations E to I. A depot based on sesame oil was used as reference.*
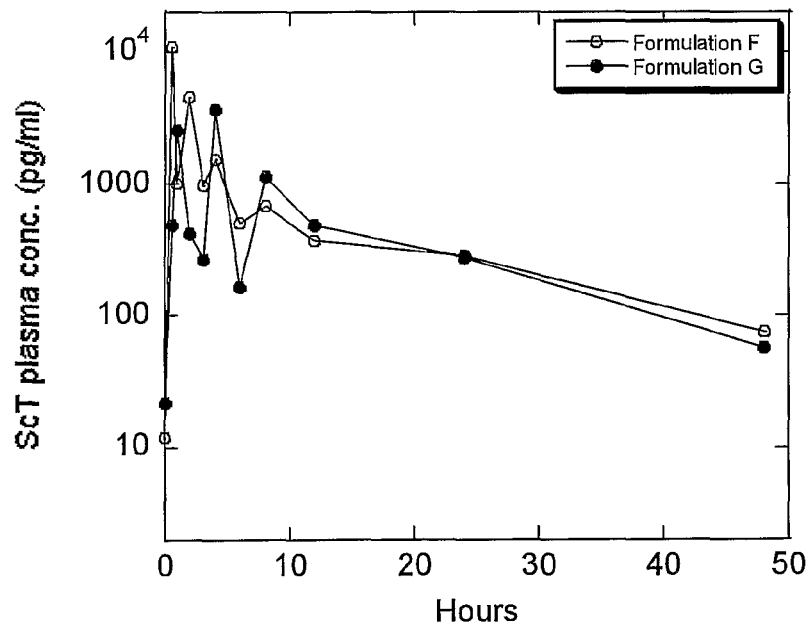
Figure 4. Plasma concentrations in the rat model after subcutaneous administration of formulations F and G.

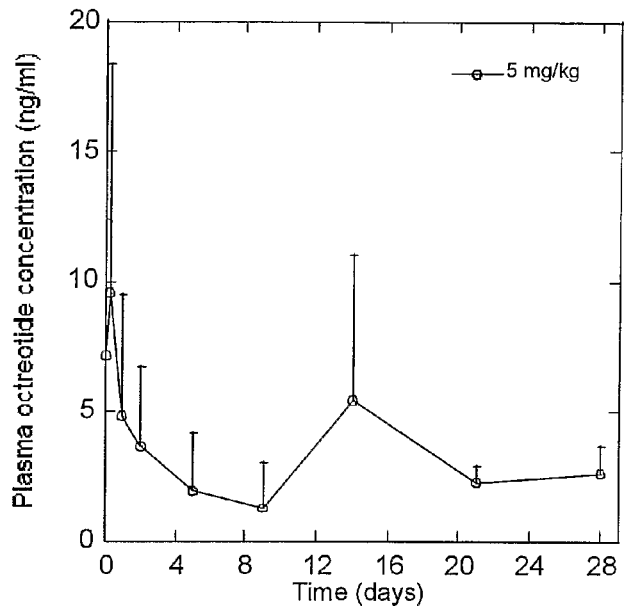
Figure 5: Octreotide plasma levels in the rat model following administration of octreotide formulation precursor (0.5% by weight octreotide).
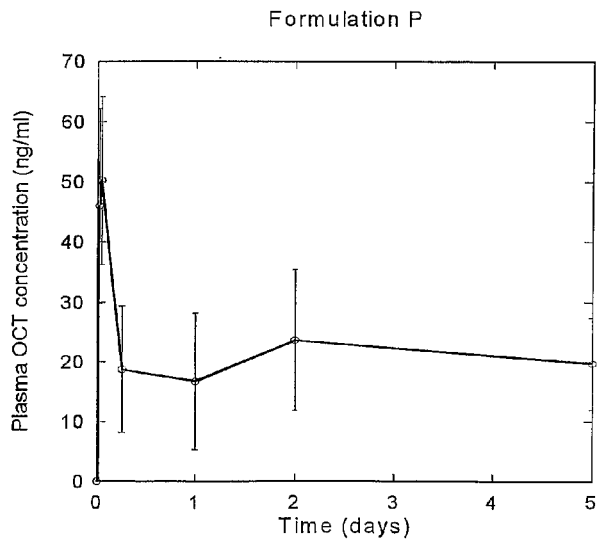
Figure 6: Octreotide plasma levels in the rat model following administration of octreotide formulation P, see Example 45.

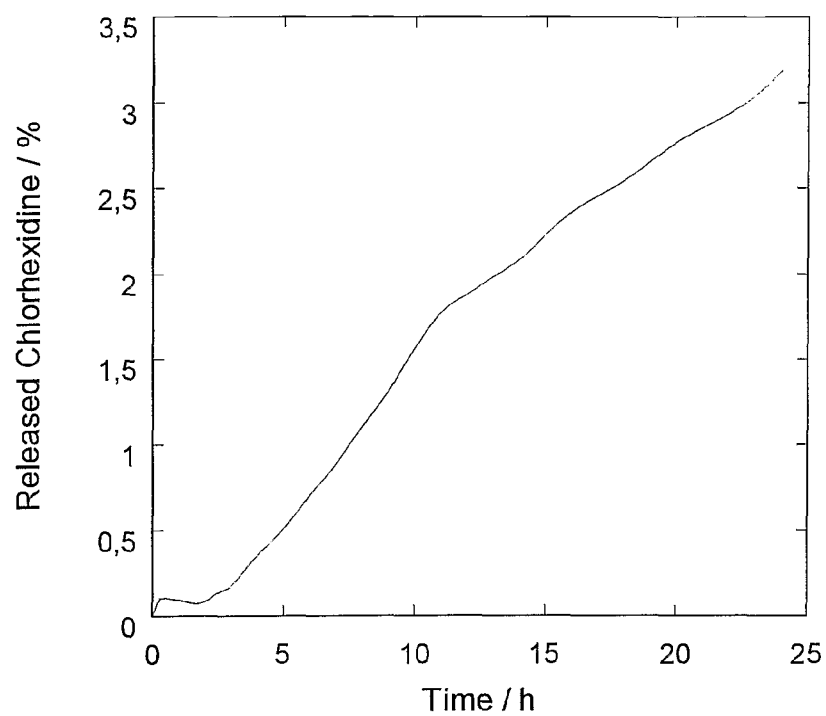
Figure 7: Release of Chlorhexidine from formulation A, see Example 47.

LIQUID DEPOT FORMULATIONS

This application is the US national phase of international application PCT/GB2005/002217, filed 6 Jun. 2005, which designated the U.S. and claims priority of GB 0412530.8, filed 4 Jun. 2004; GB 0500807.3, filed 14 Jan. 2005 and GB 0507811.8, filed 18 Apr. 2005, the entire contents of each of which are hereby incorporated by reference.

The present invention relates to formulation precursors (pre-formulations) for the in situ generation of controlled release lipid compositions. In particular, the invention relates to pre-formulations in the form of low viscosity mixtures (such as molecular solutions) of amphiphilic components and at least one bioactive agent which undergo at least one phase transition upon exposure to aqueous fluids, such as body fluids, thereby forming a controlled release matrix which optionally is bioadhesive.

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable. Furthermore, in some circumstances, such as in the fitting of implants (e.g. joint replacements or oral implants) the area of desired action may not remain accessible for repeated administration. In such cases a single administration must provide active agent at a therapeutic level over the whole period during which activity is needed.

Various method have been used and proposed for the sustained release of biologically active agents. Such methods include slow-release, orally administered compositions, such as coated tablets, formulations designed for gradual absorption, such as transdermal patches, and slow-release implants such as "sticks" implanted under the skin.

One method by which the gradual release of a bioactive agent has been proposed is a so-called "depot" injection. In this method, a bioactive agent is formulated with carriers providing a gradual release of active agent over a period of a number of hours or days. These are often based upon a degrading matrix which gradually disperses in the body to release the active agent.

The most common of the established methods of depot injection relies upon a polymeric depot system. This is typically a biodegradable polymer such poly (lactic acid) (PLA) and/or poly (lactic-co-glycolic acid) (PLGA) and may be in the form of a solution in an organic solvent, a pre-polymer mixed with an initiator, encapsulated polymer particles or polymer microspheres. The polymer or polymer particles entrap the active agent and are gradually degraded releasing the agent by slow diffusion and/or as the matrix is absorbed. Examples of such systems include those described in U.S. Pat. No. 4,938,763, U.S. Pat. No. 5,480,656 and U.S. Pat. No. 6,113,943 and can result in delivery of active agents over a period of up to several months. These systems do, however, have a number of limitations including the complexity of manufacturing and difficulty in sterilising (especially the microspheres). The local irritation caused by the lactic and/or glycolic acid which is released at the injection site is also a noticeable drawback. There is also often quite a complex procedure to prepare the injection dose from the powder precursor From a drug delivery point of view, polymer depot compositions also have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, then drop back through the bottom of the functional window during the lag period before reaching a sustained functional concentration. Evidently, from a functional and toxicological point of view this burst/lag release profile is undesirable and could be dangerous. It may also limit the equilibrium concentration which can be provided due to the danger of adverse effects at the "peak" point.

Previous depot systems have been sought to address the problem of burst release. In particular, the use of hydrolysed polylactic acid and the inclusion of poly lactic acid-polyethylene glycol block copolymers have been proposed to provide the "low burst" polymeric system described in U.S. Pat. No. 6,113,943 and U.S. Pat. No. 6,630,115. These systems provide improved profiles but the burst/lag effect remains and they do not address other issues such as the irritation caused by the use of polymers producing acidic degradation products.

One alternative to the more established, polymer based, depot systems was proposed in U.S. Pat. No. 5,807,573. This proposes a lipid based system of a diacylglycerol, a phospolipid and optionally water, glycerol, ethylene glycol or propylene glycol to provide an administration system in the reversed micellar "L2" phase or a cubic liquid crystalline phase. Since this depot system is formed from physiologically well tolerated diacyl glycerols and phospholipids, and does not produce the lactic acid or glycolic acid degradation products of the polymeric systems, there is less tendency for this system to produce inflammation at the injection site. The liquid crystalline phases are, however, of high viscosity and the L2 phase may also be too viscous for ease of application. The authors of U.S. Pat. No. 5,807,573 also do not provide any in vivo assessment of the release profile of the formulation and thus it is uncertain whether or not a "burst" profile is provided.

The use of non-lamellar phase structures (such as liquid crystalline phases) in the delivery of bioactive agents is now relatively well established. Such structures form when an amphiphilic compound is exposed to a solvent because the amphiphile has both polar and apolar groups which cluster to form polar and apolar regions. These regions can effectively solubilise both polar and apolar compounds. In addition, many of the structures formed by amphiphiles in polar and/or apolar solvents have a very considerable area of polar/apolar boundary at which other amphiphilic compounds can be adsorbed and stabilised. Amphiphiles can also be formulated to protect active agents, to at least some extent, from aggressive biological environments, including enzymes, and thereby provide advantageous control over active agent stability and release.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the L3 phase which comprises a multiply interconnected bi-continuous network of bilayer sheets which are non-lamellar but lack the long-range order of the liquid crystalline phases. Depending upon their curvature of the amphiphile sheets, these phases may be described as normal (mean curvature towards the apolar region) or reversed (mean curvature towards the polar region).

The non-lamellar liquid crystalline and L3 phases are thermodynamically stable systems. That is to say, they are not simply a meta-stable state that will separate and/or reform into layers, lamellar phases or the like, but are the stable thermodynamic form of the lipid/solvent mixture.

While the effectiveness of known lipid depot formulations is high, there are certain aspects in which the performance of these is less than ideal. In particular, cubic liquid crystalline phases proposed are relatively viscous in nature. This makes application with a standard syringe difficult, and possibly painful to the patient, and makes sterilisation by filtration impossible because the composition cannot be passed through the necessary fine-pored membrane. As a result, the compositions must be prepared under highly sterile conditions, which adds to the complexity of manufacturing. Where L2 phases are used, these are generally of lower viscosity but these may still cause difficulty in application and allow access to only a small region of the phase diagram. Specifically, the solvents used in known lipid formulations have only a limited effect in reducing the viscosity of the mixture. Water, for example, will induce the formation of a highly viscous liquid crystalline phase and solvents such as glycerol and glycols have a high viscosity and do not provide any greatly advantageous decrease in the viscosity of the composition. Glycols are also typically toxic or poorly tolerated in vivo and can cause irritation when applied topically.

Furthermore, the known lipid compositions in the low-solvent L2 phase may support only a relatively low level of many bioactive agents because of their limited solubility in the components of the mixture in the absence of water. In the presence of water, however, the formulations adopt a highly viscous cubic liquid crystalline phase. It would be a clear advantage to provide a depot system that could be injected at low viscosity and allowed release of the required concentration of bioactive with a smaller depot composition volume.

The known lipid depot compositions also have practical access to only certain phase structures and compositions because other mixtures are either too highly viscous for administration (such as those with high phospholipid concentrations) or run the risk of separation into two or more separate phases (such as an L2 phase in equilibrium with a phase rich in phospholipid). In particular, phospholipid concentrations above 50% are not reachable by known methods and from the phase diagram shown in U.S. Pat. No. 5,807,573 it appears that the desired cubic phase is stable at no higher than 40% phospholipid. As a result, it has not been possible in practice to provide depot compositions of high phospholipid concentration or having a hexagonal liquid crystalline phase structure.

The present inventors have now established that by providing a pre-formulation comprising certain amphiphilic components, at least one bioactive agent and a biologically tolerable solvent, especially in a low viscosity phase such as molecular solution, the pre-formulation may be generated addressing many of the shortfalls of previous depot formulations. In particular, the pre-formulation is easy to manufacture, may be sterile-filtered, it has low viscosity (allowing easy and less painful administration), allows a high level of bioactive agent to be incorporated (thus allowing a smaller amount of composition to be used) and/or forms a desired non-lamellar depot composition in vivo having a controllable "burst" or "non-burst" release profile. The compositions are also formed from materials that are non-toxic, biotolerable and biodegradable. Furthermore, the pre-formulation is suitable for the formation of depot compositions following parenteral administration and also following non-parenteral (e.g. topical) administration to body cavities and/or surfaces of the body or elsewhere.

In a first aspect, the present invention thus provides a pre-formulation comprising a low viscosity mixture of:
a) at least one neutral diacyl lipid and/or a tocopherol;
b) at least one phospholipid;
c) at least one biocompatible, (preferably oxygen containing) organic solvent;
wherein at least one bioactive agent is dissolved or dispersed in the low viscosity mixture and wherein the pre-formulation forms, or is capable of forming, at least one liquid crystalline phase structure upon contact with an aqueous fluid.

Generally, the aqueous fluid will be a body fluid such as fluid from a mucosal surface, tears, sweat, saliva, gastrointestinal fluid, extra-vascular fluid, extracellular fluid, interstitial fluid or plasma, and the pre-formulation will form a liquid crystalline phase structure when contacted with a body surface, area or cavity (e.g. in vivo) upon contact with the aqueous body fluid. The pre-formulation of the invention will generally not contain any significant quantity of water prior to administration.

In a second aspect of the invention, there is also provided a method of delivery of a bioactive agent to a human or non-human animal (preferably mammalian) body, this method comprising administering (preferably parenterally) a pre-formulation comprising a low viscosity mixture of:
a) at least one neutral diacyl lipid and/or a tocopherol;
b) at least one phospholipid;
c) at least one biocompatible, (preferably oxygen containing) organic solvent;
and at least one bioactive agent is dissolved or dispersed in the low viscosity mixture, whereby to form at least one liquid crystalline phase structure upon contact with an aqueous fluid in vivo following administration. Preferably, the pre-formulation administered in such a method is a pre-formulation of the invention as described herein.

The method of administration suitable for the above method of the invention will be a method appropriate for the condition to be treated and the bioactive agent used. A parenteral depot will thus be formed by parenteral (e.g. subcutaneous or intramuscular) administration while a bioadhesive non-parenteral (e.g. topical) depot composition may be formed by administration to the surface of skin, mucous membranes and/or nails, to opthalmological, nasal, oral or internal surfaces or to cavities such as nasal, rectal, vaginal or buccal cavities, the periodontal pocket or cavities formed following extraction of a natural or implanted structure or prior to insertion of an implant (e.g a joint, stent, cosmetic implant, tooth, tooth filling or other implant).

In a further aspect, the present invention also provides a method for the preparation of a liquid crystalline composition (especially a depot composition) comprising exposing a pre-formulation comprising a low viscosity mixture of:
a) at least one neutral diacyl lipid and/or a tocopherol;
b) at least one phospholipid;
c) at least one biocompatible (preferably oxygen containing), organic solvent;
and at least one bioactive agent dissolved or dispersed in the low viscosity mixture, to an aqueous fluid (particularly in vivo and/or particularly a body fluid as indicated herein). Preferably the pre-formulation administered is a pre-formulation of the present invention as described herein. The exposure to a fluid "in vivo" may evidently be internally within the body or a body cavity, or may be at a body surface such as a skin surface, depending upon the nature of the composition.

The liquid crystalline composition formed in this method is preferably bioadhesive as described herein.

In a still further aspect the present invention provides a process for the formation of a pre-formulation suitable for the administration of a bioactive agent to a (preferably mammalian) subject, said process comprising forming a low viscosity mixture of
a) at least one neutral diacyl lipid and/or a tocopherol;
b) at least one phospholipid;
c) at least one biocompatible (preferably oxygen containing), organic solvent;
and dissolving or dispersing at least one bioactive agent in the low viscosity mixture, or in at least one of components a, b or c prior to forming the low viscosity mixture. Preferably the pre-formulation so-formed is a formulation of the invention as described herein.

In a yet still further aspect the present invention provides the use of a low viscosity mixture of:
a) at least one neutral diacyl lipid and/or a tocopherol;
b) at least one phospholipid;
c) at least one biocompatible (preferably oxygen containing), organic solvent;
wherein at least one bioactive agent is dissolved or dispersed in the low viscosity mixture in the manufacture of a pre-formulation for use in the sustained administration of said active agent, wherein said pre-formulation is capable of forming at least one liquid crystalline phase structure upon contact with an aqueous fluid.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a 22 awg (or a 23 gauge) needle by manual pressure. In a particularly preferred embodiment, the low viscosity mixture should be a mixture capable of passing through a standard sterile filtration membrane such as a 0.22 μm syringe filter. In other preferred embodiments, a similar functional definition of a suitable viscosity can be defined as the viscosity of a pre-formulation that can be sprayed using a compression pump or pressurized spray device using conventional spray equipment. A typical range of suitable viscosities would be, for example, 0.1 to 5000 mPas, preferably 1 to 1000 mPas at 20° C.

It has been observed that by the addition of small amounts of low viscosity solvent, as indicated herein, a very significant change in viscosity can be provided. As indicated in FIG. 2, for example, the addition of only 5% solvent can reduce viscosity 100-fold and addition of 10% may reduce the viscosity up to 10,000 fold. In order to achieve this non-linear, synergistic effect, in lowering viscosity it is important that a solvent of appropriately low viscosity and suitable polarity be employed. Such solvents include those described herein infra.

Particularly preferred examples of low viscosity mixtures are molecular solutions and/or isotropic phases such as L2 and/or L3 phases. As describe above, the L3 is a non-lamellar phase of interconnected sheets which has some phase structure but lacks the long-range order of a liquid crystalline phase. Unlike liquid crystalline phases, which are generally highly viscous, L3 phases are of lower viscosity. Obviously, mixtures of L3 phase and molecular solution and/or particles of L3 phase suspended in a bulk molecular solution of one or more components are also suitable. The L2 phase is the so-called "reversed micellar" phase or microemulsion. Most preferred low viscosity mixtures are molecular solutions, L3 phases and mixtures thereof. L2 phases are less preferred, except in the case of swollen $L_2$ phases as described below.

The present invention provides a pre-formulation comprising components a, b, c and at least one bioactive agent as indicated herein. One of the considerable advantages of the pre-formulations of the invention is that components a and b may be formulated in a wide range of proportions. In particular, it is possible to prepare and use pre-formulations of the present invention having a much greater proportion of phospholipid to neutral, diacyl lipid and/or tocopherol than was previously achievable without risking phase separation and/or unacceptably high viscosities in the pre-formulation. The weight ratios of components a:b may thus be anything from 5:95 right up to 95:5. Preferred ratios would generally be from 90:10 to 20:80 and more preferably from 85:15 to 30:70. In one preferred embodiment of the invention, there is a greater proportion of component b than component a. That is, the weight ratio a:b is below 50:50, e.g. 48:52 to 2:98, preferably, 40:60 to 10:90 and more preferably 35:65 to 20:80.

The amount of component c in the pre-formulations of the invention will be at least sufficient to provide a low viscosity mixture (e.g. a molecular solution, see above) of components a, b and c and will be easily determined for any particular combination of components by standard methods. The phase behaviour itself may be analysed by techniques such as visual observation in combination with polarized light microscopy, nuclear magnetic resonance, and cryo-transmission electron microscopy (cryo-TEM) to look for solutions, L2 or L3 phases, or liquid crystalline phases. Viscosity may be measured directly by standard means. As described above, an appropriate practical viscosity is that which can effectively be syringed and particularly sterile filtered. This will be assessed easily as indicated herein. The maximum amount of component c to be included will depend upon the exact application of the pre-formulation but generally the desired properties will be provided by any amount forming a low viscosity mixture (e.g. a molecular solution, see above) and/or a solution with sufficiently low viscosity. Since the administration of unnecessarily large amounts of solvent to a subject is generally undesirable the amount of component c will typically be limited to no more than ten times (e.g. three times) the minimum amount required to form a low viscosity mixture, preferably no more than five times and most preferably no more than twice this amount. The composition of the present invention may, however, contain a greater quantity of solvent than would be acceptable in an immediate dosage composition. This is because the process by which the active agents are slowly released (e.g. formation of shells of liquid crystalline phase se described herein) also serve to retard the passage of solvent from the composition. As a result, the solvent is released over some time (e.g. minutes or hours) rather than instantaneously and so can be better tolerated by the body.

Higher proportions of solvent may also be used for non-parenteral (e.g. topical) applications, especially to body surfaces, where the solvent will be lost by evaporation rather than absorbed into the body. For such applications up to 100 times the minimum amount of solvent may be used (e.g. up to 95% by weight of the composition, preferably up to 80% by weight and more preferably up to 50% by weight), especially where a very thin layer of the resulting non-parenteral depot is desired.

Where the compositions of the invention are formulated as (non-parenteral) aerosol spray compositions (e.g. for topical or systemic delivery of an active), the composition may also comprise a propellant. Such compositions may also include a high proportion of solvent component c), as considered above, since much of the solvent will evaporate when the composition is dispensed.

Suitable propellants are volatile compounds which will mix with the composition of the invention under the pressure of the spray dispenser, without generating high viscosity mixtures. They should evidently have acceptable biocompatibility. Suitable propellants will readily be identified by simple testing and examples include hydrocarbons (especially $C_1$ to $C_4$ hydrocarbons), carbon dioxide and nitrogen. Volatile hydrofluorocarbons such as HFCs 134, 134a, 227ea and/or 152a may also be suitable.

As a general guide, the weight of component c will typically be around 0.5 to 50% of the total weight of the a-b-c solution. This proportion is preferably (especially for injectable depots) 2 to 30% and more preferably 5 to 20% by weight.

Component "a" as indicated herein is a neutral lipid component comprising a polar "head" group and also non-polar "tail" groups. Generally the head and tail portions of the lipid will be joined by an ester moiety but this attachment may be by means of an ether, an amide, a carbon-carbon bond or other attachment. Preferred polar head groups are non-ionic and include polyols such as glycerol, diglycerol and sugar moieties (such as inositol and glucosyl based moieties); and esters of polyols, such as acetate or succinate esters. Preferred polar groups are glycerol and diglycerol, especially glycerol.

In one preferred aspect, component a is a diacyl lipid in that it has two non-polar "tail" groups. This is generally preferable to the use of mono-acyl ("lyso") lipids because these are typically less well tolerated in vivo. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

The diacyl lipid, when used as all or part of component "a", may be synthetic or may be derived from a purified and/or chemically modified natural sources such as vegetable oils.

Mixtures of any number of diacyl lipids may be used as component a. Most preferably this component will include at least a portion of diacyl glycerol (DAG), especially glycerol dioleate (GDO). In one favoured embodiment, component a consists of DAGs. These may be a single DAG or a mixture of DAGs. A highly preferred example is DAG comprising at least 50%, preferably at least 80% and even comprising substantially 100% GDO.

An alternative or additional highly preferred class of compounds for use as all or part of component a are tocopherols. As used herein, the term "a tocopherol" is used to indicate the non-ionic lipid tocopherol, often known as vitamin E, and/or any suitable salts and/or analogues thereof. Suitable analogues will be those providing the phase-behaviour, lack of toxicity, and phase change upon exposure to aqueous fluids, which characterise the compositions of the present invention. Such analogues will generally not form liquid crystalline phase structures as a pure compound in water. The most preferred of the tocopherols is tocopherol itself, having the structure below. Evidently, particularly where this is purified from a natural source, there may be a small proportion of non-tocopherol "contaminant" but this will not be sufficient to alter the advantageous phase-behaviour or lack of toxicity. Typically, a tocopherol will contain no more than 10% of non-tocopherol-analogue compounds, preferably no more than 5% and most preferably no more than 2% by weight.

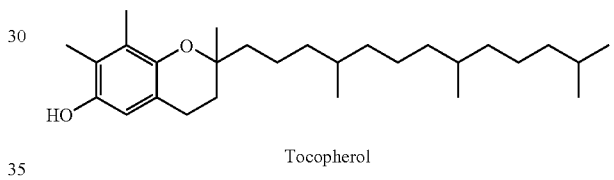

Tocopherol

In a further advantageous embodiment of the invention, component a) consists essentially of tocopherols, in particular tocopherol as shown above.

A preferred combination of constituents for component a) is a mixture of at least one DAG (e.g. GDO) with at least one tocopherol. Such mixtures include 2:98 to 98:2 by weight tocopherol:GDO, e.g. 10:90 to 90:10 tocopherol:GDO and especially 20:80 to 80:20 of these compounds. Similar mixtures of tocopherol with other DAGs are also suitable.

Component "b" in the present invention is at least one phospholipid. As with component a, this component comprises a polar head group and at least one non-polar tail group. The difference between components a and b lies principally in the polar group. The non-polar portions may thus suitably be derived from the fatty acids or corresponding alcohols considered above for component a. It will typically be the case that the phospholipid will contain two non-polar groups, although one or more constituents of this component may have one non-polar moiety. Where more than one non-polar group is present these may be the same or different.

Preferred phospholipid polar "head" groups include phosphatidylcholine, phosphatidylethanolamine, phosphatidylserine and phosphatidylinositol. Most preferred is phosphatidylcholine (PC). In a preferred embodiment, component b) thus consists of at least 50% PC, preferably at least 70% PC and most preferably at least 80% PC. Component b) may consist essentially of PC.

The phospholipid portion, even more suitably than any diacyl lipid portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids.

Since the pre-formulations of the invention are to be administered to a subject for the controlled release of an active agent, it is preferable that the components a and b are biocompatible. In this regard, it is preferable to use, for example, diacyl lipids and phospholipids rather than monoacyl (lyso) compounds. A notable exception to this is tocopherol, as described above. Although having only one alkyl chain, this is not a "lyso" lipid in the convention sense. The nature of tocopherol as a well tolerated essential vitamin evidently makes it highly suitable in biocompatibility.

It is furthermore most preferable that the lipids and phospholipids of components a and b are naturally occurring (whether they are derived from a natural source or are of synthetic origin). Naturally occurring lipids tend to cause lesser amounts of inflammation and reaction from the body of the subject. Not only is this more comfortable for the subject but it may increase the residence time of the resulting depot composition, especially for parenteral depots, since less immune system activity is recruited to the administration site. In certain cases it may, however, be desirable to include a portion of a non-naturally-occurring lipid in components a and/or b. This might be, for example an "ether lipid" in which the head and tail groups are joined by an ether bond rather than an ester. Such non-naturally-occurring lipids may be used, for example, to alter the rate of degradation of the resulting depot-composition by having a greater or lesser solubility or vulnerability to breakdown mechanisms present at the site of active agent release. Although all proportions fall within the scope of the present invention, generally, at least 50% of each of components a and b will be naturally occurring lipids. This will preferably be at least 75% and may be up to substantially 100%.

Two particularly preferred combinations of components a and b are GDO with PC and tocopherol with PC, especially in the region 30-90 wt % GDO/tocopherol, 10-60 wt % PC and 1-30% solvent (especially ethanol, NMP and/or ispropanol).

In addition to amphiphilic components a and b, the preformulations of the invention may also contain additional amphiphilic components at relatively low levels. In one embodiment of the invention, the pre-formulation contains up to 10% (by weight of components a and b) of a charged amphiphile, particularly an anionic amphiphile such as a fatty acid. Preferred fatty acids for this purpose include caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable fatty acids are palmitic, stearic, oleic and linoleic acids, particularly oleic acid. It is particularly advantageous that this component be used in combination with a cationic peptide active agent (see below). The combination of an anionic lipid and a cationic peptide is believed to provide a sustained release composition of particular value. This may in part be due to increased protection of the peptide from the degradative enzymes present in vivo.

Component "c" of the pre-formulations of the invention is an oxygen containing organic solvent. Since the pre-formulation is to generate a depot composition following administration (e.g. in vivo), upon contact with an aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

In a preferred version, the solvent is such that a relatively small addition to the composition comprising a and b, i.e. below 20%, or more preferably below 10%, give a large viscosity reductions of one order of magnitude or more. As described herein, the addition of 10% solvent can give a reduction of two, three or even four orders of magnitude in viscosity over the solvent-free composition, even if that composition is a solution or $L_2$ phase containing no solvent, or an unsuitable solvent such as water (subject to the special case considered below), or glycerol.

Typical solvents suitable for use as component c include at least one solvent selected from alcohols, ketones, esters (including lactones), ethers, amides and sulphoxides. Examples of suitable alcohols include ethanol, isopropanol and glycerol formal.

Monools are preferred to diols and polyols. Where diols or polyols are used, this is preferably in combination with an at least equal amount of monool or other preferred solvent. Examples of ketones include acetone, n-methyl pyrrolidone (NMP), 2-pyrrolidone, and propylene carbonate. Suitable ethers include diethylether, glycofurol, diethylene glycol monoethyl ether, dimethylisobarbide, and polyethylene glycols. Suitable esters include ethyl acetate and isopropyl acetate and dimethyl sulphide is as suitable sulphide solvent. Suitable amides and sulphoxides include dimethylacetamide (DMA) and dimethylsulphoxide (DMSO), respectively. Less preferred solvents include dimethyl isosorbide, tetrahydrofurfuryl alcohol, diglyme and ethyl lactate.

Since the pre-formulations are to be administered to a living subject, it is necessary that the solvent component c is sufficiently biocompatible. The degree of this biocompatibility will depend upon the application method and since component c may be any mixture of solvents, a certain amount of a solvent that would not be acceptable in large quantities may evidently be present. Overall, however, the solvent or mixture forming component c must not provoke unacceptable reactions from the subject upon administration. Generally such solvents will be hydrocarbons or preferably oxygen containing hydrocarbons, both optionally with other substituents such as nitrogen containing groups. It is preferable that little or none of component c contains halogen substituted hydrocarbons since these tend to have lower biocompatibility. Where a portion of halogenated solvent such as dichloromethane or chloroform is necessary, this proportion will generally be minimised. Where the depot composition is to be formed non-parenterally a greater range of solvents may evidently be used than where the depot is to be parenteral.

Component c as used herein may be a single solvent or a mixture of suitable solvents but will generally be of low viscosity. This is important because one of the key aspects of the present invention is that it provides preformulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c (single solvent or mixture) should typically be no more than 18 mPas at 20° C. This is preferably no more than 15 mPas, more preferably no more than 10 mPas and most preferably no more than 7 mPas at 20° C.

The solvent component c will generally be at least partially lost upon in vivo formation of the depot composition, or diluted by absorption of water from the surrounding air and/or tissue. It is preferable, therefore, that component c be at least to some extent water miscible and/or dispersible and at least should not repel water to the extent that water absorption is prevented. In this respect also, oxygen containing solvents with relatively small numbers of carbon atoms (for example up to 10 carbons, preferably up to 8 carbons) are preferred. Obviously, where more oxygens are present a solvent will tend to remain soluble in water with a larger number of carbon atoms. The carbon to heteroatom (e.g. N, O, preferably oxygen) ratio will thus often be around 1:1 to 6:1, preferably 2:1 to 4:1. Where a solvent with a ratio outside one of these preferred ranges is used then this will preferably be no more than 75%, preferably no more than 50%, in combination with a preferred solvent (such as ethanol). This may be used, for example to decrease the rate of evaporation of the solvent from the pre-formulation in order to control the rate of liquid crystalline depot formation.

A further advantage of the present pre-formulations is that a higher level of bioactive agent may be incorporated into the system. In particular, by appropriate choice of components a-c (especially c), high levels of active agent may be dissolved or suspended in the pre-formulations. Generally, the lipid components in the absence of water are relatively poorly solubilising but in the presence of water form phases too viscous to administer easily. Higher proportions of bioactive agent may be included by use of appropriate solvents as component c and this level will either dissolve in the depot composition as it forms in situ or may form microdrops or microcrystals which will gradually dissolve and release active agent. A suitable choice of solvent will be possible by routine experimentation within the guidelines presented herein.

The pre-formulations of the present invention typically do not contain significant amounts of water. Since it is essentially impossible to remove every trace of water from a lipid composition, this is to be taken as indicating that only such minimal trace of water exists as cannot readily be removed. Such an amount will generally be less than 1% by weight, preferably less that 0.5% by the weight of the pre-formulation. In one preferred aspect, the pre-formulations of the invention do not contain glycerol, ethylene glycol or propylene glycol and contain no more than a trace of water, as just described.

There is, however, a certain embodiment of the present invention in which higher proportions of water may be tolerated. This is where water is present as a part of the solvent component in combination with an additional water-miscible component c (single solvent or mixture). In this embodiment, up to 10 wt % water may be present providing that at least 3 wt %, preferably at least 5% and more preferably at least 7 wt % component c is also present, that component c is water miscible, and that the resulting preformulation remains non-viscous and thus does not form a liquid crystalline phase. Generally there will be a greater amount of component c) by weight than the weight of water included in the preformulation. Most suitable solvents of use with water in this aspect of the invention include ethanol, isopropyl alcohol, NMP, acetone and ethyl acetate.

The pre-formulations of the present invention contain one or more bioactive agents (described equivalently as "active agents" herein). Active agents may be any compound having a desired biological or physiological effect, such as a protein, drug, antigen, nutrient, cosmetic, fragrance, flavouring, diagnostic, pharmaceutical, vitamin, or dietary agent and will be formulated at a level sufficient to provide an in vivo concentration at a functional level (including local concentrations for topical compositions). Under some circumstances one or more of components a, b and/or c may also be an active agent, although it is preferred that the active agent should not be one of these components. Most preferred active agents are pharmaceutical agents including drugs, vaccines, and diagnostic agents.

Drug agents that may be delivered by the present invention include drugs which act on cells and receptors, peripheral nerves, adrenergic receptors, cholinergic receptors, the skeletal muscles, the cardiovascular system, smooth muscles, the blood circulation system, endocrine and hormone system, blood circulatory system, synoptic sites, neuroeffector junctional sites, the immunological system, the reproductive system, the skeletal system, autacoid system, the alimentary and excretory systems, the histamine system, and the central nervous system.

Examples of drugs which may be delivered by the composition of the present invention include, but are not limited to, antibacterial agents such as β-lactams or macrocyclic peptide antibiotics, anti fungal agents such as polyene macrolides (e.g. amphotericin B) or azole antifungals, anticancer and/or anti viral drugs such as nucleoside analogues, paclitaxel and derivatives thereof, anti inflammatorys, such as non-steroidal anti inflammatory drugs and corticosteroids, cardiovascular drugs including cholesterol lowering and blood-pressure lowing agents, analgesics, antipsychotics and antidepressants including seritonin uptake inhibitors, prostaglandins and derivatives, vaccines, and bone modulators. Diagnostic agents include radionuclide labelled compounds and contrast agents including X-ray, ultrasound and MRI contrast enhancing agents. Nutrients include vitamins, coenzymes, dietary supplements etc.

Particularly suitable active agents include those which would normally have a short residence time in the body due to rapid breakdown or excretion and those with poor oral bioavailability. These include peptide, protein and nucleic acid based active agents, hormones and other naturally occurring agents in their native or modified forms. By administering such agents in the form of a depot composition formed from the pre-formulation of the present invention, the agents are provided at a sustained level for a length of time which may stretch to days, weeks or even several months in spite of having rapid clearance rates. This offers obvious advantages in terms of stability and patient compliance over dosing multiple times each day for the same period. In one preferred embodiment, the active agent thus has a biological half life (upon entry into the blood stream) of less than 1 day, preferably less than 12 hours and more preferably less than 6 hours. In some cases this may be as low as 1-3 hours or less. Suitable agents are also those with poor oral bioavailability relative to that achieved by injection, for where the active agent also or alternatively has a bioavailability of below 0.1%, especially below 0.05% in oral formulations.

Peptide and protein based active agents include human and veterinary drugs selected from the group consisting of adrenocorticotropic hormone (ACTH) and its fragments, angiotensin and its related peptides, antibodies and their fragments, antigens and their fragments, atrial natriuretic peptides, bioadhesive peptides, Bradykinins and their related peptides, calcitonins and their related peptides, cell surface receptor protein fragments, chemotactic peptides, cyclosporins, cytokines, Dynorphins and their related peptides, endorphins and P-lidotropin fragments, enkephalin and their related proteins, enzyme inhibitors, immunostimulating peptides and polyaminoacids, fibronectin fragments and their related peptides, gastrointestinal peptides, gonadotrophin-releasing hormone (GnRH) agonists and antagonist, glucagons like peptides, growth hormone releasing peptides, immunostimulating peptides, insulins and insulin-like growth factors, interleukins, luthenizing hormone releasing hormones (LRH) and their related peptides, melanocyte stimulating hormones and their related peptides, nuclear localization signal related peptides, neurotensins and their related peptides, neurotransmitter peptides, opioid peptides, oxytocins, vasopressins and their related peptides, parathyroid hormone and its fragments, protein kinases and their related peptides, somatostatins and their related peptides, substance P and its related peptides, transforming growth factors (TGF) and their related peptides, tumor necrosis factor fragments, toxins and toxoids and functional peptides such as anticancer peptides including angiostatins, antihypertension peptides, anti-blood clotting peptides, and antimicrobial peptides; selected from the group consisting of proteins such as immunoglobulins, angiogenins, bone morphogenic proteins, chemokines, colony stimulating factors (CSF), cytokines, growth factors, interferons (Type I and II), interleukins, leptins, leukaemia inhibitory factors, stem cell factors, transforming growth factors and tumor necrosis factors.

A further considerable advantage of the depot compositions of the present invention is that active agents are released gradually over long periods without the need for repeated dosing. The composition are thus highly suitable for situations where patient compliance is difficult, unreliable or where a level dosage is highly important, such as mood-altering actives, those actives with a narrow therapeutic window, and those administered to children or to people who's lifestyle is incompatible with a reliable dosing regime. Also for "lifestyle" actives where the inconvenience of repeated dosing might outweigh the benefit of the active. Particular classes of actives for which this aspect offers a particular advantage include contraceptives, hormones including contraceptive hormones, and particularly hormones used in children such as growth hormone, anti-addictive agents, supplements such as vitamin or mineral supplements, antidepressants and anticonvulsants Cationic peptides are particularly suitable for use where a portion of the pre-formulation comprises an anionic amphiphile such as a fatty acid. In this embodiment, preferred peptides include octreotide, lanreotide, calcitonin, oxytocin, interferon-beta and -gamma, interleukins 4, 5, 7 and 8 and other peptides having an isoelectric point above pH 7, especially above pH 8.

In one preferred aspect of the present invention, the composition of the invention is such that an $I_2$ phase, or a mixed phase including $I_2$ phase is formed upon exposure to aqueous fluids and a polar active agent is included in the composition.

Particularly suitable polar active agents include peptide and protein actives, oligo nucleotides, and small water soluble actives, including those listed above. Of particular interest in this aspect are the peptide octreotide and other somatostatin related peptides, interferons alpha and beta, glucagon-like peptides 1 and 2, luprorelin and other GnRH agonist, abarelix and other GnRH antagonists, interferon alpha and beta, zolendronate and ibandronate and other bisphosponates, and polar active chlorhexidine (e.g. chlorhexidine digluconate or chlorhexidine dihydrochloride).

A particular advantage of the present invention when used in combination with protein/peptide active agents is that aggregation of the active agent is suppressed. In one preferred embodiment, the present invention thus provides a depot precursor and particularly a depot composition as described herein comprising at least one peptide (e.g. antibody) or protein active agent wherein no more than 5% of the active agent is in aggregated form. Preferably no more than 3% is aggregated and most preferably no more than 2% (especially less than 2%) is in aggregated form. This stabilisation of non-aggregated protein is highly advantageous from the point of view of high effectiveness, low side effects and predictable absorption profile. Furthermore, it is increasingly expected that protein/peptide therapeutics will have low levels of protein aggregation in order to secure regulatory approval.

The amount of bioactive agent to be formulated with the pre-formulations of the present invention will depend upon the functional dose and the period during which the depot composition formed upon administration is to provide sustained release. Typically, the dose formulated for a particular agent will be around the equivalent of the normal daily dose multiplied by the number of days the formulation is to provide release. Evidently this amount will need to be tailored to take into account any adverse effects of a large dose at the beginning of treatment and so this will generally be the maximum dose used. The precise amount suitable in any case will readily be determined by suitable experimentation.

In one embodiment, the pre-formulations of the present invention will generally be administered parenterally. This administration will generally not be an intra-vascular method but will preferably be subcutaneous intracavitary or intramuscular. Typically the administration will be by injection, which term is used herein to indicate any method in which the formulation is passed through the skin, such as by needle, catheter or needle-less injector.

In parenteral (especially sub cutaneous) depot precursors, preferred active agents are those suitable for systemic administration including antibacterials (including amicacin, monocycline anddoxycycline), local and systemic anagesics (including bupivacain, tramadol, fentanyl, morphine, hydromorphone, methadone, oxycodone, codeine, asperine, acetaminophen), NSAIDS (such as ibuprofene, naproxene, keteprofene, indomethansine, sulindac, tolmethin, salysylic acids such as salisylamide, diflunisal), Cox1 or Cox2 inhibitors (such as celecoxib, rofecoxib, valdecoxib) anticancer agents (including octreotide, lanreotide, buserelin, luprorelin, goserelin, triptorelin, avorelin, deslorein, abarelix, degarelix, fulvestrant, interferon alpha, interferon beta, darbepoetin alpha, epoetin alpha, beta, delta, and paclitaxel), antipsychotics (like bromperidol, risperidone, olanzapine, iloperidone, paliperadone, pipotiazine and zuclopenthixol), antivirals, anticonvulsants (for instance tiagabine topiramate or gabapentin) or nicotine, hormones (such as testosterone, and testosterone undecanoate, medroxyprogesterone, estradiol) growth hormones (like human growth hormone), and growth factors (like granulocyte macrophage colony-stimulating factor)

In an alternative embodiment, the formulations of the present invention may form non-parenteral depots where the active agent is slowly released at a body surface. It is especially important in this embodiment that the pre-formulations of the invention and/or the liquid crystalline depot compositions formed therefrom should preferably be bioadhesive. That is to say that the compositions should coat the surface to which they are applied and/or upon which they form as appropriate and should remain even when this surface is subject to a flow of air or liquid and/or rubbing. It is particularly preferable that the liquid crystalline depot compositions formed should be stable to rinsing with water. For example, a small volume of depot precursor may be applied to a body surface and be exposed to a flow of five hundred times its own volume of water per minute for 5 minutes. After this treatment, the composition can be considered bioadhesive if less than 50% of the bioactive agent has been lost. Preferably this level of loss will be matched when water equaling 1000 times and more preferably 10 000 times the volume of the composition is flowed past per minute for five, or preferably 10, minutes.

Although the non-parenteral depot compositions of the present invention may absorb some or all of the water needed to form a liquid crystalline phase structure from the biological surfaces with which they are contacted, some additional water may also be absorbed from the surrounding air. In particular, where a thin layer of high surface area is formed then the affinity of the composition for water may be sufficient for it to form a liquid crystalline phase structure by contact with the water in the air. The "aqueous fluid" are referred to herein is thus, at least partially, air containing some moisture in this embodiment.

Non-parenteral depot compositions will typically be generated by applying the pre-formulation topically to a body surface or to a natural or artificially generated body cavity and/or to the surface of an implant. This application may be by direct application of liquid such as by spraying, dipping, rinsing, application from a pad or ball roller, intra-cavity injection (e.g to an open cavity with or without the use of a needle), painting, dropping (especially into the eyes) and similar methods. A highly effective method is aerosol or pump spraying and evidently this requires that the viscosity of the pre-formulation be as low as possible and is thus highly suited to the compositions of the invention. Non-parenteral depots may, however, be used to administer systemic agents e.g. transmucosally or transdermally.

Non-parenteral depots may also be used for application to surfaces, particularly of implants and materials which will be in contact with the body or a body part or fluid. Devices such as implants, catheters etc. may thus be treated e.g. by dipping or spraying with the preformulations of the invention, which will form a robust layer to reduce the introduction of infection. Anti-infective actives are particularly suited to this aspect.

Conditions particularly suitable for causative or symptomatic treatment by topical bioadhesive depot compositions of the present invention include skin conditions (such as soreness resulting from any cause including chapping, scratching and skin conditions including eczema and herpes) eye conditions, genital soreness (including that due to genital infection such as genital herpes), infections and conditions for the finger and/or toe nails (such as bacterial or fungal infections of the nails such as onychomycosis or poronychia). Topical-type bioadhesive formulations may also be used to administer systemic active agents (e.g. medication), particularly by skin adsorption, oral, transdermal or rectal routes. Travel sickness medication is a preferred example, as is nicotine (e.g. in anti-smoking aids). Where context permits, "topical application" as referred to herein includes systemic agents applied non-parenterally to a specific region of the body.

Periodontal infections are particularly suitable for treatment by the compositions of the present invention. In particular, known compositions for treating periodontal infection are difficult to apply or are generally ineffective. The most widely used periodontal depot composition comprises insertion of a collagen "chip" into the periodontal space, from which an anti-infective agent is released. This chip is difficult to insert and does not form to match the shape and volume of the periodontal space, so that pockets of infection may remain untreated. In contrast to this, the compositions of the present invention, applied as a low viscosity preformulation, can be easily and quickly injected into the periodontal space and will flow to conform exactly to that space and fill the available volume. The compositions then quickly absorb water to form a robust gel which is resistant to aqueous conditions of the mouth. The only known previous attempt at such an injectible periodontal treatment relied on dispersions of relatively high viscosity which were difficult to apply and were subject to undesirable phase separation. All of these drawbacks are now addressed in the compositions of the present invention as described herein. Highly suitable actives for periodontal administration are antiinfectives, especially benzydamine, tramadol and chlorhexidine.

Non-parenteral depot compositions are also of significant benefit in combination with non-pharmaceutical active agents, such as cosmetic actives, fragrances, essential oils etc. Such non-pharmaceutical depots will maintain the important aspects of bioadhesion and sustained release to provide prolonged cosmetic effects, but may easily be applied by spraying or wiping. This additionally applies to agents which have both cosmetic and medical (especially prophylactic) benefits such as sun-protective agents. Since the topical depot compositions provide robust, water resistant barriers which can solubilise high levels of actives, they are especially suitable for sunscreens and sunblocks in combination with ultra violet light (UV, e.g. UVa, Uvb and/or UVc) absorbing and/or scattering agents, particularly where high levels of protection is desirable. The compositions are furthermore highly biocompatible and may act to moisten and soothe the skin during sun exposure. Compositions of the invention containing soothing agents such as aloe vera are also highly suitable for soothing and moistening application after exposure to sunlight, or to skin which is dry, inflamed or damaged due to, for example irritation, burning or abrasion.

Active agents particularly suited to non-parenteral (e.g. topical) depot administration, which comprises intra oral, buccal, nasal, ophthalmic, dermal, vaginal delivery routes, include antibacterials such as chlorhexidine, chloramphenicol, triclosan, tetracycline, terbinafine, tobramycin, fusidate sodium, butenafine, metronidazole (the latter particularly for the (e.g. symtomatic) treatment of acne rosacea—adult acne or some vaginal infections), antiviral, including acyclovir, anti infectives such as bibrocathol, ciprofloxacin, levofloxacin, local analgesics such as benzydamine, lidocaine, prilocaine, xylocaine, bupivacaine, analgesics such as tramadol, fentanyl, morphine, hydromorphone, methadone, oxycodone, codeine, asperine, acetaminophen, NSAIDS such as ibuprofen, flurbiprofen, naproxene, ketoprofen, fenoprofen, diclofenac, etodalac, diflunisal, oxaproxin, piroxicam, piroxicam, indomethansine, sulindac, tolmethin, salysylic acids such as salisylamide and diflunisal, Cox1 or Cox2 inhibitors such as celecoxib, rofecoxib or valdecoxib, corticosteroids, anticancer and immuno stimulating agents (for instance, metylaminolevulinat hydrocloride, interferon alpha and beta), anticonvulsants (for instance tiagabine topiramate or gabapentin), hormones (such as testosterone, and testosterone undecanoate, medroxyprogesterone, estradiol) growth hormones (like human growth hormone), and growth factors (like granulocyte macrophage colony-stimulating factor), immuno suppressants (cyclosporine, sirolimus, tacrolimus), nicotine and antivirals (e.g. acyclovir).

Some specific actives found by the inventors to form highly effective depots of the present invention include the following:

For long acting injectable depot products of hydrophilic active agents;
i. octreotide (or other somatostatin analogues such as lanreotide for treatment of carcoid and VIP producing tumours and acromegali). Subcutaneous depots formable, especially with GDO and PC having a sustained release duration of more than one month and showing less than 20% octreotide degraded in one month in water-swollen depot at 37° C. Surprisingly good stability was observed and found to be better than octreotide formulated in microspheres. Depot showed less than 5% degradation in product preformulation over eight weeks at 4° C.

ii. human growth hormone. For treatment of growth disorders and growth hormone deficiencies. Subcutaneous depot formable, especially with GDO and PC having a sustained release duration of more than two weeks iii. interferon alpha, for treatment of cancer and viral infections. Subcutaneous depots formable, especially with GDO and PC, having a sustained release duration of more than one month iv. leuprolide. Depots formable having continuous delivery (preferably continuous delivery inside therapeutic window) for minimum of one month.

For long acting injectable depots of lipophilic/amphiphilic actives;

i. risperidone
ii. olanzapine
iii. testosterone undecanoate

Depots i to iii formable having continuous delivery (preferably continuous delivery inside therapeutic window) for minimum of two weeks.

For topical bioadhesive, controlled release products for intraoral (including buccal & periodontal) administration;

i. benzydamine (local analgesic, anti inflammatory,) or other local analgesic, analgesic, anti inflammatory, anti bacterial, anti fungal or combination thereof. Composition provides sustained effect at intraoral mucosa, in particular damaged, sensitised, infected mucosa e.g. in patients suffering from oral mucositis (induced by e.g. chemo- and radiotherapy). In particular for treatment of oral mucositis.

ii. tramadol (analgesic). Provides a composition with sustained systemic analgesic effect.

iii. chlorhexidine gluconate (antibacterial) for treatment of periodontal and topical infections. Particularly for long acting effect in periodontal pocket.

Compositions result in depots releasing chlorhexidine over more than 1 h, preferably more than 6 h, most preferably more than 24 h when applied as a liquid, forming a bioadhesive gel in situ. Surface gel formation time observed to be between 1 second and 5 min.

Depots i to iii formable having high level of active agent incorporation and high degree of resistance to washing away. Preformulations in the form of a liquid administered as spray or liquid wash/rinse for i and ii and gel-forming liquid for iii, wherein liquid is applied to periodontal pocket, e.g. by injection.

For non-parenteral (e.g. topical or systemic) bioadhesive, controlled release products for nasal administration;

i. fentanyl (analgesic) provides rapid onset and sustained duration analgesia when administered as spray ii. diazepam (anti anxiety) provides non-parenteral, nasal depot with systemic effect giving rapid onset and sustained duration. Administered as a spray For topical bioadhesive, controlled release products for ophthalmic administration;

i. diclofenac (NSAID) with sustained duration. Administered as in situ phase forming liquid ii. pilocarpine (parasymptomimetic, cholinergic agonist) for treatment of glaucoma.

iii. levocabastine hydrochloride, ketotifen fumarate providing liquid for eye-dropping to give long lasting relief from allergic conjunctivitis with long period between reapplication.

iv. Pilocarpine hydrochloride for the treatment of Sjögrens syndrome.

v. dexamethasone, (corticosteroid)

vi. chloramphenicol (primarily bacteriostatic antiinfective)

vii. indomethacin (NSAID)

Depots i to vii formulated as liquid spray or more preferably drops for direct application to eye surface and provide in situ depot formation with high resistance to washing out by tears and wear from blinking/eye rubbing.

Other actives suitable for ophthalmic compositions include Antihistamines, Mast cell stabilizers, Nonsteroidal anti-inflammatory drugs (NSAIDs), Corticosteroids (e.g. to treat allergic conjunctivitis), Anti-Glaucoma actives including inflow suppressing/inhibiting agents (beta blocking agents: timolol, betaxolol, carteolol, levobunolol, etc., topical carbonic anhydrase inhibitors: dorzolamide, brinzolamide, sympathomimetics: epinephrine, dipivefrin, clonidine, apraclonidine, brimonidine), outflow facilitating agents (parasympathomimetics (cholinergic agonists): pilocarpine prostaglandin analogues and related compounds: atanoprost, travoprost, bimatoprost, unoprostone)

For non-parenteral (e.g. topical or systemic) bioadhesive, controlled release products for dermatological administration;

i. acyclovir (antiviral). Composition generates a bioadhesive, film forming product with sustained duration. Applied as spray or liquid ii. testosterone undecanoate (hormone deficiency). bioadhesive, film forming composition with sustained duration. May be applied as aerosol- or pump-spray, or as liquid.

Particularly suitable applications of dermatological formulations are anti-infective dermatological bioadhesive depots for protection in environments where contact with infective agents likely (e.g. human or veterinary surgery, abattoir work, certain types of cleaning etc.). Bioadhesive depots generated from composition of the invention provide robust and sustained protection for the wearer. The compositions with anti-infective agents may also be used in situations where skin sterility of the wearer is important for the health of others, such as for nurses or doctors visiting multiple patients in hospital, where cross-infection must be avoided. A prior coating with a composition of the present invention may serve to provide resistance against picking up of infectives from one area and thus prevent transmission to another.

The pre-formulations of the present invention provide non-lamellar liquid crystalline depot compositions upon exposure to aqueous fluids, especially in vivo and in contact with body surfaces. As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. By use of the pre-formulations of the present invention it is possible to generate any phase structure present in the phase-diagram of components a and b with water. This is because the pre-formulations can be generated with a wider range of relative component concentrations than previous lipid depot systems without risking phase separation or resulting in highly viscous solutions for injection. In particular, the present invention provides for the use of phospholipid concentrations above 50% relative to the total amphiphile content. This allows access to phases only seen at high phospholipid concentrations, particularly the hexagonal liquid crystalline phases.

For many combinations of lipids, only certain non-lamellar phases exist, or exist in any stable state. It is a surprising feature of the present invention that compositions as described herein frequently exhibit non-lamellar phases which are not present with many other combinations of components. In one particularly advantageous embodiment, therefore, the present invention relates to compositions having a combination of components for which an $I_2$ and/or $L_2$ phase region exists when diluted with aqueous solvent. The presence or absence of such regions can be tested easily for any particular combination by simple dilution of the composition with aqueous solvent and study of the resulting phase structures by the methods described herein.

In a highly advantageous embodiment, the compositions of the invention may form an $I_2$ phase, or a mixed phase including $I_2$ phase upon contact with water. The $I_2$ phase is a reversed cubic liquid crystalline phase having discontinuous aqueous regions. This phase is of particular advantage in the controlled release of active agents and especially in combination with polar active agents, such as water soluble actives because the discontinuous polar domains prevent rapid diffusion of the actives. Depot precursors in the $L_2$ are highly effective in combination with an $I_2$ phase depot formation. This is because the $L_2$ phase is a so-called "reversed micellar" phase having a continuous hydrophobic region surrounding discrete polar cores. $L_2$ thus has similar advantages with hydrophilic actives. In transient stages after contact with body fluid the composition can comprise multiple phases since the formation of an initial surface phase will retard the passage of solvent into the core of the depot, especially with substantial sized administrations of internal depots. Without being bound by theory, it is believed that this transient formation of a surface phase, especially a liquid crystalline surface phase, serves to dramatically reduce the "burst/lag" profile of the present compositions by immediately restricting the rate of exchange between the composition and the surroundings. Transient phases may include (generally in order from the outside towards the centre of the depot): $H_{II}$ or $L_\alpha$, $I_2$, $L_2$, and liquid (solution). It is highly preferred that the composition of the invention is capable forming at least two and more preferably at least three of these phases simultaneously at transient stages after contact with water at physiological temperatures. In particular, it is highly preferred that one of the phases formed, at least transiently, is the $I_2$ phase.

It is important to appreciate that the preformulations of the present invention are of low viscosity. As a result, these pre-formulations must not be in any bulk liquid crystalline phase since all liquid crystalline phases have a viscosity significantly higher than could be administered by syringe or spray dispenser. The preformulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 10 wt % of solvent (component c) having a viscosity reducing effect. This is in contrast to a "concentrated" or "unswollen" $L_2$ phase containing no solvent, or a lesser amount of solvent, or containing a solvent (or mixture) which does not provide the decrease in viscosity associated with the oxygen-containing, low viscosity solvents specified herein.

Upon administration, the pre-formulations of the present invention undergo a phase structure transition from a low viscosity mixture to a high viscosity (generally tissue adherent) depot composition. Generally this will be a transition from a molecular mixture, swollen $L_2$ and/or L3 phase to one or more (high viscosity) liquid crystalline phases such as normal or reversed hexagonal or cubic liquid crystalline phases or mixtures thereof As indicated above, further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. up to 30 minutes, preferably up to 10 minutes, more preferably 5 minutes of less). The remainder of the composition may change phase to a liquid crystalline phase more slowly by diffusion and/or as the surface region disperses.

In one preferred embodiment, the present invention thus provides a pre-formulation as described herein of which at least a portion forms a hexagonal liquid crystalline phase upon contact with an aqueous fluid. The thus-formed hexagonal phase may gradually disperse, releasing the active agent, or may subsequently convert to a cubic liquid crystalline phase, which in turn then gradually disperses. It is believed that the hexagonal phase will provide a more rapid release of active agent, in particular of hydrophilic active agent, than the cubic phase structure, especially the $I_2$ and $L_2$ phase. Thus, where the hexagonal phase forms prior to the cubic phase, this will result in an initial release of active agent to bring the concentration up to an effective level rapidly, followed by the gradual release of a "maintenance dose" as the cubic phase degrades. In this way, the release profile may be controlled.

Without being bound by theory, it is believed that upon exposure (e.g. to body fluids), the pre-formulations of the invention lose some or all of the organic solvent included therein (e.g. by diffusion and/or evaporation) and take in aqueous fluid from the bodily environment (e.g. moist air close to the body or the in vivo environment) such that at least a part of the formulation generates a non-lamellar, particularly liquid crystalline phase structure. In most cases these non-lamellar structures are highly viscous and are not easily dissolved or dispersed into the in vivo environment and are bioadhesive and thus not easily rinsed or washed away. Furthermore, because the non-lamellar structure has large polar, apolar and boundary regions, it is highly effective in solubilising and stabilising many types of active agents and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

It is an unexpected finding of the present inventors that the pre-formulations result in a depot composition that have very little "burst" effect in the active agent release profile. This is unexpected because it might be expected that the low viscosity mixture (especially if this is a solution) of the pre-composition would rapidly lose active agent upon exposure to water. In fact, pre-formulations of the invention have shown considerably less of an initial "burst" than previously known polymer-base depot compositions. This is illustrated in the Examples below and Figures attached hereto. In one embodiment, the invention thus provides injectable preformulations and resulting depot compositions wherein the highest plasma concentration of active after administration is no more than 5 times the average concentration between 24 hours and 5 days of administration. This ratio is preferably no more than 4 times and most preferably no more than 3 times the average concentration.

In an additional aspect of the invention, the topical compositions may be used to provide a physical barrier on body surfaces, in the absence of any active agent. In particular, because of the very high bioadherance of the compositions, "barrier" coatings formed by spraying or application of liquid may be formed from the present compositions so as to reduce contact with potential infective or irritant agents or to reduce soiling of the body surfaces. The robust nature of the compositions and resistance to washing provide advantageous characteristics for such barriers, which could conveniently be applied as a liquid or by spraying.

The Invention will now be further illustrated by reference to the following non-limiting Examples and the attached Figures, in which;

FIG. 1 shows the cumulative release of methylene blue (MB) from a depot formulation comprising PC/GDO/EtOH (45/45/10 wt %) when injected into excess water;

FIG. 2 demonstrates the non-linear decrease of pre-formulation viscosity upon addition of N-methyl pyrolidinone (NMP) and EtOH;

FIG. 3 shows the plasma concentration (in rats) of salmon calcitonin (sCT) after subcutaneous injection of various PC/GDO/EtOH depot precursors containing 500 µg sCT/g of formulation;

FIG. 4 shows the initial in vivo release (up to 48 hours) to plasma (in rats) of sCT from two different depot formulations following subcutaneous injection;

FIG. 5 shows the plasma concentration (in rats) of octreotide (OCT) following subcutaneous injection of a depot formulation comprising PC/GDO/EtOH (36/54/10 wt %) containing 5 mg OCT/g formulation, corresponding to 0.5% drug load.

FIG. 6 shows the plasma concentration (in rats) of octreotide (OCT) following subcutaneous injection of a depot formulation comprising PC/GDO/EtOH (47.5/47.5/5.0 wt %) containing 30 mg OCT/g formulation, corresponding to 3% drug load.

FIG. 7 displays the in vitro release in excess aqueous phase of chlorhexidine from a depot formulation comprising PC/GDO/EtOH (36/54/10 wt %) containing 50 mg chlorhexidine/g of formulation, corresponding to 5% drug load.

EXAMPLES

Example 1

Availability of Various Liquid Crystalline Phases in the Depot by Choice of Composition Injectable formulations containing different proportions of phosphatidyl choline ("PC"—Epikuron 200) and glycerol dioleate (GDO) and with EtOH as solvent were prepared to illustrate that various liquid crystalline phases can be accessed after equilibrating the depot precursor formulation with excess water.

Appropriate amounts of PC and EtOH were weighed in glass vials and the mixture was placed on a shaker until the PC completely dissolved to form a clear liquid solution. GDO was then added to form an injectable homogenous solution.

Each formulation was injected in a vial and equilibrated with excess water. The phase behaviour was evaluated visually and between crossed polarizes at 25° C. Results are presented in Table 1.

TABLE 1

| Formulation | PC (wt %) | GDO (wt %) | EtOH (wt %) | Phase in H$_2$O |
|---|---|---|---|---|
| A | 22.5 | 67.5 | 10.0 | L$_2$ |
| B | 28.8 | 61.2 | 10.0 | I$_2$ |
| C | 45.0 | 45.0 | 10.0 | H$_{II}$ |
| D | 63.0 | 27.0 | 10.0 | H$_{II}$/L$_\alpha$ |

L$_2$ = reversed micellar phase
I$_2$ = reversed cubic liquid crystalline phase
H$_{II}$ = reversed hexagonal liquid crystalline phase
L$_\alpha$ = lamellar phase Example 2

In Vitro Release of a Water-Soluble Substance

A water-soluble colorant, methylene blue (MB) was dispersed in formulation C (see Example 1) to a concentration of 11 mg/g formulation. When 0.5 g of the formulation was injected in 100 ml water a stiff reversed hexagonal H$_{II}$ phase was formed. The absorbency of MB released to the aqueous phase was followed at 664 nm over a period of 10 days. The release study was performed in an Erlenmeyer flask at 37° C. and with low magnetic stirring.

The release profile of MB (see FIG. 1) from the hexagonal phase indicates that this (and similar) formulations are promising depot systems. Furthermore, the formulation seems to give a low initial burst, and the release profile indicates that the substance can be released for several weeks; only about 50% of MB is released after 10 days.

Example 3

Viscosity in PC/GDO (6:4) or PC/GDO (3:7) on Addition of Solvent (EtOH, PG and NMP)

A mixture of PC/GDO/EtOH was manufactured according to the method in Example 1. All, or nearly all, of the EtOH was removed from the mixture with a rotary evaporator (vacuum, 40° C., 1 h) and the resulting solid mixture were weighed in glass vial after which 2, 5, 10 or 20% of a solvent (EtOH, propylene glycol (PG) or n-methyl pyrrolidone (NMP)) was added. The samples were allowed to equilibrate several days before the viscosity was measured at a shear rate of 0.1 s$^{-1}$ with a Physica UDS 200 rheometer at 25° C.

This example clearly illustrates the need for solvent with certain depot precursors in order to obtain an injectable formulation (see FIG. 2). The viscosity of solvent-free PC/GDO mixtures increases with increasing ratio of PC. Systems with low PC/GDO ratio (more GDO) are injectable with a lower concentration of solvent.

Example 4

Composition and In Vitro Phase Study

The formulations were manufactured according to the method described in Example 1 with compositions according to Table 2. An active substance (peptide), salmon calcitonin (sCT), was added to each formulation to a concentration of 500 µg sCT/g formulation. The formulations were designed as homogenous suspensions for parenteral administration (mixing required shortly prior to use since the drug is not completely dissolved in the PC/GDO/EtOH system).

The phase study in this example is performed in excess of rat serum at 37° C. in order to simulate an in vivo situation. Table 2 shows that the same phases as those in water are formed (compare Table 1).

TABLE 2

| Formulation | PC (wt %) | GDO (wt %) | OA (wt %) | EtOH (wt %) | Phase in rat serum |
|---|---|---|---|---|---|
| E | 18 | 72 | — | 10 | $L_2$ |
| F | 36 | 54 | — | 10 | $I_2$ |
| G | 34 | 51 | 5 | 10 | $I_2$ |
| H | 54 | 36 | — | 10 | $H_{II}$ |
| I | 72 | 18 | — | 10 | $H_{II}/L_\alpha$ |

OA = Oleic Acid

Example 5

Sterile Filtration of Formulations with Reduced Viscosity

To lower the viscosity with various solvents is sometimes necessary in order to obtain an injectable formulation and to be able to administrate the system with a regular syringe (see Example 3). Another important effect from the viscosity-lowering solvent is that the formulations can be sterile filtrated.

Formulations E to I in Example 4 were studied in a sterile filtration test by using a 0.22 μm filter (before addition of the active substance). Formulations E to H were successfully filtrated, but formulation I failed since the viscosity was too high. An aseptic manufacturing procedure was therefore needed for this formulation.

Example 6

In Vivo Release Study from Depot Formulations Subcutaneously Administered

Formulations E to I in Example 4 were used in an in vivo drug release study in rat. The formulations were administrated subcutaneously between the scapulae by using a syringe (21G, 0.6 mm×30 mm) and the dose of sCT was 500 μg/kg body weight. The release profile was monitored for a period of 13 days. The sCT concentration in the rat plasma samples was analysed with sandwich-type immunoassay using a commercial kit from DSLabs.

FIG. 3 shows the results (n=4). A pure triglyceride vehicle based on sesame oil was selected as a lipid reference system.

Example 7

In Vivo Release Study in the Initial Phase

Formulations F and G as in Example 6 were used in an in vivo study in rat designed to investigate the initial "burst effect". From FIG. 4 (n=8) it appears that none of the investigated formulations has a severe burst effect.

Example 8

Preparation of Depot Precursor Compositions with Various Solvents

Depending on composition of the formulation and the nature and concentration of active substance certain solvents may be preferable.

Depot precursor formulations (PC/GDO/solvent (36/54/10)) were prepared by with various solvents; NMP, PG, PEG400, glycerol/EtOH (90/10) by the method of Example 1. All depot precursor compositions were homogeneous one phase solutions with a viscosity that enabled injection through a syringe (23G—i.e. 23 gauge needle; 0.6 mm×30 mm). After injecting formulation precursors into excess water a liquid crystalline phase in the form of a high viscous monolith rapidly formed with NMP and PG containing precursors. The liquid crystalline phase had a reversed cubic micellar ($I_2$) structure. With PEG400, glycerol/EtOH (90/10) the viscosification/solidification process was much slower and initially the liquid precursor transformed to a soft somewhat sticky piece. The difference in appearance probably reflects the slower dissolution of PEG400 and glycerol towards the excess aqueous phase as compared to that of EtOH, NMP and PG.

Example 9

Preparation of Depot Composition Containing Human Growth Hormone (HGH)

Human growth hormone (hGH) plays a critical role in stimulating body growth and development, and is involved in the production of muscle protein and in the breakdown of fats. A deficiency of the hormone adversely affects numerous body processes such as lipid profile, insulin status, physical performance, bone-mineral density and quality of life. A targeted dose every 2 weeks is estimated at 0.10 to 0.24 mg/kg of body weight.

1 ml of a 2 weeks depot formulation precursor was formed by sequentially mixing 10 mg hGH and 360 mg PC in 0.1 ml NMP. 540 mg GDO was added to the mixture to obtain a low viscosity depot formulation precursor. Injecting the formulation precursor into excess water (syringe 23G; 0.6 mm×30 mm) resulted in a monolithic liquid crystalline phase ($I_2$ structure).

Example 10

Preparation of Depot Composition Containing a Sparingly Soluble Active Substance Risperidone is an antipsychotic medication agent belonging to the chemical class of benzisoxazole derivatives. It is a very strong dopamine blocker (antagonist); ie, it inhibits functioning of dopamine receptors, it is practically insoluble in water, and it has log(P)=3.49.

1 g of a depot formulation containing 50 mg of risperidone was prepared by dissolving the active, substance in 0.7 g of a mixture 95% wt in EtOH (99.5%) and 5% wt in acetic acid. 0.34 g PC and 0.51 g GDO were subsequently dissolved in this solution followed by solvent reduction to remaining 0.15 g solvent (0.55 g was evaporated under vacuum). The composition of the final homogenous and clear depot formulation with 50 mg risperidone was PC/GDO/solvent/risperidone (32/49/14/5). Injecting the formulation precursor into excess water (syringe 23 G; 0.6 mm×30 mm) resulted in a monolithic liquid crystalline phase ($I_2$ structure). I.e. the amount of active substance (5%) did not change monolith formation and phase behavior after exposure to an aqueous environment.

Example 11

Alternate Preparation of Depot Composition Containing Risperidone

A risperidone depot precursor formulation could also be prepared by using a solvent mixture composed of 90% wt EtOH (99.5%) and 10% wt in acetic acid.

50 mg of risperidone was dissolved in 0.7 g of the solvent mixture, after which 0.36 g PC and 0.54 g GDO were subsequently dissolved in this solution. 0.60 g of the solvent mixture was evaporated under vacuum to a homogenous and clear depot formulation precursor with 50 mg risperidone (PC/GDO/solvent/risperidone (34/51/10/5)). Injecting the formulation precursor into excess water (syringe 23 G; 0.6 mm×30 mm) resulted in a monolithic liquid crystalline phase ($I_2$ structure). I.e. the amount of active substance (5%) did not change monolith formation and phase behavior after exposure to an aqueous environment.

Example 12

Temperature Stability of Depot Composition Containing a Sparingly Soluble Active Substance The risperdone depot precursor formulations in examples 10 and 11 were tested for stability against crystallization during storage. Each formulation was stable at 25° C. for at least two weeks and at +8° C. for at least one week.

Example 13

Preparation of Depot Composition Containing Benzydamine

Benzydamine is a non-steroidal antiinflammatory drug and is extensively used as a topical drug in inflammatory conditions.

1 g of a depot formulation containing 1.5 mg benzydamine was prepared by dissolving the active substance in a mixture of PC/GDO/EtOH (36/54/10) prepared as described in Example 1. The depot composition was stable against crystallization during storage at 25° C. for at least two weeks. Equilibration of the formulation precursor with excess water resulted in a high viscous monolithic liquid crystalline phase (I2 structure).

Example 14

Robustness of the Behaviour of the Formulation Against Variations in the Excipient Quality Depot precursor formulations were prepared with several different GDO qualities (supplied by Danisco, Dk), Table 3, using the method of Example 1. The final depot precursors contained 36% wt PC, 54% wt GDO, and 10% wt EtOH. The appearance of the depot precursors was insensitive to variation in the quality used, and after contact with excess water a monolith was formed with a reversed micellar cubic phase behaviour ($I_2$ structure).

TABLE 3

Tested qualities of GDO.

| GDO quality | Monoglyceride (% wt) | Diglyceride (% wt) | Triglyceride (% wt) |
|---|---|---|---|
| A | 10.9 | 87.5 | 1.6 |
| B | 4.8 | 93.6 | 1.6 |
| C | 1.0 | 97.3 | 1.7 |
| D | 10.1 | 80.8 | 10.1 |
| E | 2.9 | 88.9 | 8.2 |
| F | 0.9 | 89.0 | 10.1 |

Example 15

Preparation of Depot Composition Containing Saturated PC (Epikuron 200SH)

Depot precursor formulations were prepared with various amounts PC comprising saturated hydrocarbon chains by addition of Epikuron 200SH directly to a mixture of PC/GDO/EtOH, prepared as for Example 1. The formulations are shown in Table 4. All precursor formulations were homogenous one phase samples in RT, while they became more viscous with increasing amount Epikuron 200SH. Injecting the depot precursor into excess water gave a monolith comprising a reversed miceller cubic ($I_2$) structure. Monoliths formed from samples containing higher amounts of Epikuron 200SH became turbid, possibly indicating segregation between Epikuron 200SH and the other components upon exposure to water and formation of the I2 phase.

TABLE 4

Depot composition containing saturated PC

| Formulation | Saturated PC, Epikuron 200SH (% wt) | PC (% wt) | GDO (% wt) | EtOH (% wt) |
|---|---|---|---|---|
| G1 | 3.9 | 34.6 | 51.9 | 9.6 |
| G2 | 7.0 | 33.5 | 50.2 | 9.3 |
| G3 | 14.3 | 30.8 | 46.3 | 8.6 |

Example 16

Preparation of Depot Precursor being a Dispersion or Solution of the Peptide Salmon Calcitonin By adding 500 µg sCT/g formulation to a solution of PC/GDO/EtOH (36/54/10), obtained as in Example 1, a dispersion of sCT was formed.

In an alternative method, 500 µg sCT was dissolved in excess of EtOH followed by addition of PC and GDO. The solvent concentration was then reduced (EtOH evaporation) to form a homogenous (active drug in solution) formulation. This latter technique can be used to obtain higher drug loads. Precursor compositions corresponding to at least 1500 µg dissolved sCT per gram of the final depot precursor composition could be obtained by this method.

Example 17

In Vivo Release Study from Depot Formulation Subcutaneously Administered

The two sCT compositions described in Example 16 were administered in an in vivo rat model by subcutaneous injection (between the scapulae). The first depot precursor having dispersed sCT was found to give somewhat unstable initial plasma concentrations, while the second depot precursor, having sCT dissolved therein, gave much more stable initial plasma levels (see Table 5).

TABLE 5

| Formulations | Coefficient of variation (% CV) |
|---|---|
| Dispersed: 500 µg sCT/g PC/GDO/EtOH (36/54/10) | 32-127 |
| Dissolved: 500 µg sCT/g PC/GDO/EtOH (36/54/10) | 20-37 |

Example 18

Preparation of Depot Composition Containing the Peptide Octreotide

Octreotide is an acetate salt of a synthetic octa-peptide and is similar to the hormone somatostatin. Octreotide decreases production of substances such as growth hormone, insulin and glucagons. It is used in treatment of acromegaly, and to reduce flushing and watery diarrhoea caused by metastatic cancerous tumors (carcinoid syndrome) or tumors called vasoactive intestinal peptide tumors (VIPomas).

24 mg or 60 mg octreotide was dissolved in 0.1 g EtOH. 0.36 g PC and 0.54 g GDO were subsequently dissolved in this solution and a depot formulation precursor was obtained. Injecting the formulation precursor into excess aqueous phase (syringe 23 G; 0.6 mm×30 mm) resulted in a monolithic liquid crystalline phase ($I_2$ structure). I.e. octreotide (2.4% or 6.0%) did not change monolith formation and phase behaviour after exposure to an aqueous environment.

The octreotide depot precursor formulations in this Example were tested for stability against crystallization during storage. Each formulation was stable at 4-8° C. for at least two weeks.

Example 19

In Vivo Release Study from Depot Formulation Containing Octreotide Subcutaneously Administered In an in vivo rat model the drug release of octreotide was followed during 28 days. The formulations were administered subcutaneously between the scapulae by using a syringe (23 G, 0.6 mm×25 mm). The octreotide concentration in the rat plasma was followed for a period of 28 days (see FIG. 5). The dose was 5 mg/kg and volume 1 ml/kg corresponding to a drug load of 0.5% octreotide in the depot formulation precursor (PC/GDO/EtOH (36/54/10)).

From FIG. 5 (n=3) it appears that the investigated formulation gives a release profile essentially without a burst effect.

FIG. 5 shows Octreotide plasma levels in the rat model following administration of octreotide formulation precursor (0.5% in octreotide).

Example 20

Degradation of Depot Formulation in the Rat

Various volumes (1, 2, 6 ml/kg) of the depot precursor (36% wt PC, 54% wt GDO, and 10% wt EtOH) were injected in the rat and were removed again after a period of 14 days. It was found that substantial amounts of the formulations were still present subcutaneously in the rat after this time, see Table 6.

TABLE 6

Mean diameter of depot monolith.

| Dose (ml/kg) | Mean diameter day 3 (mm) | Mean diameter day 14 (mm) |
|---|---|---|
| 1 (n = 3) | 15.8 | 12.5 |
| 2 (n = 3) | 18.5 | 15.3 |
| 6 (n = 3) | 23.3 | 19.3 |

Example 21

In Vitro Study of Formation of Depot Monolith after Injection of Depot Formulation Precursor Between the Bone and Periostium A precursor (36% wt PC, 54% wt GDO, and 10% wt EtOH prepared as described in Example 1) was injected by syringe between the bone and periostium. The composition was observed to spread to fill voids and after uptake of aqueous fluids formed a monolith that was bioadhesive to both the bone and periostium.

Example 22

Bioadhesive Spray of Depot Precursor Formulation

A pump spray bottle was found to be a convenient way to apply the formulation topically, e.g. to the skin or the oral mucosa.

A depot precursor formulation prepared as in Example 1 (36% wt PC, 54% wt GDO, and 10% wt EtOH) was sprayed with a pump spray bottle onto the skin and oral mucosa. A film with solid mechanical properties formed shortly after application.

Example 23

Robustness of a Topical Film

After applying the depot precursor formulation, as described in Example 22, (36% wt PC, 54% wt GDO, and 10% wt EtOH) to the skin, the applied formulation was exposed to flushing water (10 L/min) for 10 minutes. The formulation showed excellent bioadhesive properties and resistance against rinsing and no loss of the formulation could be discerned.

Example 24

Formation of Cubic Phase with Solid Properties after Exposure of Depot Precursor Formulation to Air After exposing a depot precursor formulation prepared as described in Example 1 (36% wt PC, 54% wt GDO, and 10% wt EtOH) to air (RT, relative humidity 40%) for at least 3 hours, a solid cubic phase was formed. This formation of a cubic phase structure demonstrates that a topical film will acquire bulk non-lamellar depot properties after application without the need for direct exposure to excess aqueous fluid.

Example 25

Formulation to Treat Periodontitis or Perimplantitis

In order to treat periodontitis or perimplantitis an antibacterial formulation is injected in the periodontal pocket, and a prolonged effect of the formulation is normally desired.

100 μL of a formulation as prepared in Example 1, with the addition of the antibiotic chlorhexidine (PC/GDO/EtOH/chlorhexidine (35/53/10/2)), is injected via a syringe into a rat peridontal pocket. The injected composition is observed to transform from the low viscous formulation, and which initially spreads out to fill voids, to form a solid mass by uptake of gingival fluids. An antibacterial depot system is thus provided.

Chlorhexidine remains at clinically effective levels (MIC 125 µg/ml) in the GCF of the periodontal pockets for over 1 week. The depot system is completely degraded by enzymes within 7 to 10 days and does not need to be removed.

Example 26

Alternate Antibacterial Formulation to Treat Periodontitis or Perimplantitis

An alternate antibacterial formulation was provided by a formulation prepared as described in Example 1 and containing the antibacterial detergent Gardol (Glycine, N-methyl-N-(1-oxododecyl)-, sodium salt) (PC/GDO/EtOH(Gardol (34/51/10/5)). This formulation is injected into the rat periodontal pocket.

Gardol is observed to remain at clinically effective levels in the GCF of the periodontal pockets for a prolonged period (several days). The depot system is completely degraded by enzymes within 7 to 10 days and did not need to be removed.

Example 27

Adhesion of the Formulation to High Energy Surfaces

In order to treat perimplantitis, adhesion not only to biological surfaces but also to high energy surfaces such as a gold or titanium implant is important. It is also important that the formulation adheres to ceramic and plastic surfaces.

A formulation (PC/GDO/EtOH (36/54/10)) as prepared in Example 1 was applied to various surfaces in the oral cavity. The composition showed excellent adhesion to ceramic, plastic, gold, as well as to a normal tooth surface and could not be rinsed away by excess aqueous fluid. The depot resulting from the composition stayed at the site in the oral cavity where it was applied for at least 6 h.

Example 28

Bioadhesive Sustained Release Formulation of Sodium Fluoride for use on the Teeth Fluoride containing compounds are often needed to oppose caries attack and a bioadhesive formulation precursor with depot effect was prepared as indicated in Example 1 from a mixture of PC/GDO/EtOH/sodium fluoride (35/53/10/2). The formulation was a dispersion of sodium fluoride since it could not be dissolved in the precursor. The liquid formulation was applied to the teeth with the aid of a brush. By uptake of saliva the formulation solidified and formed a depot providing sustained release of sodium fluoride for an extended period (several hours).

Example 29

Oral Cavity Spray Depot Composition

To be suitable as a topical depot system in the oral cavity the mechanical properties of the system was adjusted by decreasing the PC/GDO ratio.

A mixture containing PC/GDO/EtOH (27/63/10) was prepared according to Example 1. A drop of patent blue was added to visualize the formulation after application. About 300 µl of the formulation was sprayed into the oral cavity with pump spray bottle. Shortly after application the formulation viscosified/solidified since it underwent a phase transformation by uptake of aqueous fluid (saliva) and loss of solvent (EtOH). The formulation had excellent bioadhesion to keritinized surfaces such as the hard palate and the gum. Here the film lasted for several hours despite saliva secretion and mechanical wear by the tongue. At soft mucosal surfaces the duration was much shorter (minutes).

Example 30

Oral Cavity Liquid Depot Composition

To be suitable for application with a pipette to the oral cavity the solidification/viscosification of the formulation has to be delayed relative to the spray formulation. This is to allow the formulation to be conveniently distributed with the tongue to a thin film in the oral cavity after application.

Propylene glycol (PG) and EtOH were added to a formulation prepared as in Example 1, to the final composition PC/GDO/EtOH/PG (24/56/10/10). 300 µl of the formulation was conveniently applied with a pipette to the oral cavity and distributed with the tongue to a thin film in the oral cavity. After about 20 seconds the viscosification of the formulation started since it underwent a phase transformation by uptake of aqueous fluid (saliva) and loss of solvent (EtOH and PG). After about one minute the solidification/viscosification appeared to be finished. The formulation had excellent bioadhesion to keritinized surfaces such as the hard palate and the gum. Here the film lasted for several hours despite saliva secretion and mechanical wear by the tongue. At soft mucosal surfaces the duration was much shorter (minutes).

Example 31

Bioadhesive Depot for Nails

The mixture in Example 29 was sprayed to the nail bed and in between the toes. The formulation solidifies/viscosifies slowly by uptake of aqueous fluids (cf. sweat). The solidification can be speeded up by adding water after spray application. The formulation had excellent bioadhesive properties and had a duration for several hours.

Example 32

Loading Capacity of the Bioactive Agent Benzydamine in the Formulation Precursors Formulations with compositions as specified in Table 7 were prepared using the method in Example 1. An excess amount of benzydamine (50 mg) was added to 0.5 g of the formulations. The vials were placed on a shaker at 15° C. for three days after which the solutions were filtered through a filter (0.45 µm) to get rid of crystals of undissolved benzydamine. The benzydamine concentration in each formulation was determined with reversed phase gradient HPLC and UV detection at 306 nm and the results are given in Table 7.

TABLE 7

| Composition GDO/PC (Lipoid S100)/EtOH | Benzydamine concentration in formulation |
|---|---|
| 67.5/22.5/10 | 3.4% |
| 63/27/10 | 3.2% |
| 58.5/31.5/10 | 3.3% |
| 60/20/20 | 4.0% |
| 56/24/20 | 4.5% |
| 52/28/20 | 4.3% |

Example 33

Compositions Containing PC and Tocopherol

Depot precursor formulations were prepared with several different PC/α-tocopherol compositions using the method of Example 1 (PC was first dissolved in the appropriate amount of EtOH and thereafter α-tocopherol was added to give clear homogenous solutions).

Each formulation was injected in a vial and equilibrated with excess water. The phase behaviour was evaluated visually and between crossed polarizes at 25° C. Results are presented in Table 8.

TABLE 8

| α-tocopherol | PC | Ethanol | Phase in excess H$_2$O |
|---|---|---|---|
| 2.25 g | 2.25 g | 0.5 g | H$_{II}$ |
| 2.7 g | 1.8 g | 0.5 g | H$_{II}$/I$_2$ |
| 3.15 g | 1.35 g | 0.5 g | I$_2$ |
| 3.6 g | 0.9 g | 0.5 g | I$_2$/L$_2$ |

Example 34

Composition Containing Octreotide 60 mg octreotide was dissolved in 0.1 g EtOH. 0.25 g PC and 0.59 g α-tocopherol were subsequently dissolved in this solution and a depot formulation precursor was obtained. Injecting the formulation precursor into excess aqueous solution (phosphate buffered saline—PBS) resulted in a monolithic liquid crystalline phase (I$_2$ structure) i.e. octreotide (6.0%) did not change monolith formation and phase behaviour after exposure to an aqueous environment.

The octreotide depot precursor formulation in this Example was tested for stability against crystallization during storage. The formulation was stable at 4-8° C. for at least two weeks.

Example 35

In Vitro Release of Water-Soluble Disodium Fluorescein

A water-soluble colorant, disodium fluorescein (Fluo), was dissolved in a formulation containing PC/α-tocopherol/Ethanol (27/63/10 wt %) to a concentration of 5 mg Fluo/g formulation. When 0.1 g of the formulation was injected in 2 ml of phosphate buffered saline (PBS) a reversed micellar (I$_2$) phase was formed. The absorbency of Fluo released to the aqueous phase was followed at 490 nm over a period of 3 days. The release study was performed in a 3 mL vial capped with an aluminium fully tear off cap at 37° C. The vial was placed on a shaking table at 150 rpm.

The release of Fluo from the PC/α-tocopherol formulation (see Table 9) indicates that this (and similar) formulations are promising depot systems. Furthermore, the absence of a burst effect is noteworthy, and the release indicates that the substance can be released for several weeks to months; only about 0.4% of Fluo is released after 3 days.

TABLE 9

| | % release (37° C.) | |
|---|---|---|
| Formulation | 24 h | 72 h |
| PC/α-tocopherol/EtOH: 27/63/10 wt % | <0.1* | 0.43 |

*Release below detection limit of the absorbance assay

Example 36

Formulations of the Analgesic/Antiinflammatory Benzydamine

Formulations were prepared as in Example 1 by mixing benzydamine with a mixture of GDO, PC, ethanol and optionally PG/AP in the following proportions.

| Formulation | BZD | GDO | PC | EtOH | PG | AP |
|---|---|---|---|---|---|---|
| 1 | 3.0 | 53.3 | 28.7 | 10.0 | 5.0 | 0.01 |
| 2 | 3.0 | 53.3 | 28.7 | 15.0 | 0 | 0.01 |
| 3 | 3.0 | 57.4 | 24.6 | 10.0 | 5.0 | 0.01 |
| 4 | 3.0 | 49.2 | 32.8 | 10.0 | 5.0 | 0.01 | where BZD is benzydamine, EtOH is ethanol, PC is LIPOID S100 soybean phosphatidylcholine, GDO is glycerol dioleate, PG is propylene glycol, and AP is ascorbyl palmitate.

All formulations are low viscosity liquids which generate liquid crystalline phase compositions upon exposure to aqueous conditions.

Example 37

Fentanyl Nasal Formulation

Formulations were prepared as in Example 1 by mixing the narcotic analgesic fentanyl with a mixture of GDO, PC, ethanol and optionally PG in the following proportions.

| Formulation | Fentanyl | PC | GDO | EtOH | PG |
|---|---|---|---|---|---|
| 1 | 0.05 | 34 | 51 | 10 | 5 |
| 2 | 0.05 | 36 | 54 | 10 | — |
| 3 | 0.05 | 42 | 43 | 10 | 5 |
| 4 | 0.05 | 45 | 45 | 10 | — |
| 5 | 0.15 | 34 | 51 | 10 | 5 |
| 6 | 0.15 | 36 | 54 | 10 | — |
| 7 | 0.05 | 30 | 45 | 15 | 10 |
| 8 | 0.15 | 30 | 45 | 15 | 10 | where EtOH is ethanol, PC is LIPOID S100 soybean phosphatidylcholine, GDO is glycerol dioleate, and PG is propylene glycol All formulations are low viscosity liquids suitable for administration by nasal spray, which generate liquid crystalline phase compositions upon exposure to aqueous conditions.

Example 38

Diazepam Nasal Formulation

Formulations were prepared as in previous examples by mixing the benzodiazepine antianxiety agent diazepam with a mixture of GDO, PC, ethanol and optionally PG in the following proportions.

| Formulation | Diazepam | PC | GDO | EtOH | PG |
|---|---|---|---|---|---|
| 1 | 5 | 32 | 48 | 10 | 5 |
| 2 | 5 | 34 | 51 | 10 | — |
| 3 | 10 | 37 | 38 | 10 | 5 |
| 4 | 10 | 40 | 40 | 10 | — |
| 5 | 10 | 30 | 45 | 10 | 5 |
| 6 | 10 | 32 | 48 | 10 | — |
| 7 | 10 | 26 | 39 | 15 | 10 |
| 8 | 10 | 30 | 45 | 15 | — | where EtOH is ethanol, PC is LIPOID S100 soybean phosphatidylcholine, GDO is glycerol dioleate, and PG is propylene glycol All formulations are low viscosity liquids suitable for administration by nasal spray, which generate liquid crystalline phase compositions upon exposure to aqueous conditions.

Example 39

Interferon Alpha-2a

Interferons (IFNs) are used as a treatment for many types of systemic cancer, often in combination with chemotherapy or radiation. Recent data suggest that IFN Alpha is a multifunctional immunomodulatory cytokine with profound effects on the cytokine cascade including several anti-inflammatory properties. These newly identified immunoregulatory and anti-inflammatory functions may also be of importance in treatment of diseases such as chronic viral hepatitis and help to explain some of the IFN mechanisms.

A non-aqueous precursor formulation was formed by dissolving PC (360 mg) and GDO (540 mg) in EtOH (100 mg). Interferon Alpha-2a (4 mg) was dissolved in water (76 mg) and this solution was thereafter added to the non-aqueous precursor formulation to form a depot formulation precursor of low viscosity.

Injecting the depot precursor into excess water (syringe 23 G; 0.6 mm×30 mm) resulted in a monolithic liquid crystalline phase ($I_2$ structure).

Example 40

Leuprorelin (Leuprolide)

Leuprorelin acetate (or leuprolide acetate) is a synthetic nonapeptide analogue of naturally occurring gonadotropin releasing hormone (GnRH or LH-RH) that, when given continuously (e.g. as a depot formulation), inhibits pituitary gonadotropin secretion and suppresses testicular and ovarion steroidogenesis. Leuprorelin is used for the treatment of advanced prostate cancer.

A depot formulation precursor was formed by sequentially dissolving 22.5 mg leuprorelin acetate and 360 mg PC in 100 mg of NMP. 540 mg of GDO was added to the mixture yielding a molecular solution depot formulation precursor of low viscosity. Injecting the formulation precursor into excess water (syringe 23 G; 0.6 mm×30 mm) resulted in a monolithic liquid crystalline phase ($I_2$ structure).

Example 41

Alendronate

Bisphosphonates are structural analogues of pyrophosphates and have pharmacologic activity specific for bone due to the strong affinity of bisphosphonates for hydroxyapatite, a major inorganic component of bone. The compounds are used to treat postmenopausal osteoporosis, hypercalcemia of malignancy and metastatic bone disease (MBD).

A non-aqueous precursor formulation was formed by dissolving PC (360 mg) and GDO (540 mg) in EtOH (100 mg). Alendronate (12 mg) was dissolved in water (80 mg) and this solution was thereafter added to the non-aqueous precursor formulation to form a depot formulation precursor of low viscosity. Injecting the depot precursor into excess water (syringe 23 G; 0.6 mm×30 mm) resulted in a monolithic liquid crystalline phase ($I_2$ structure).

Example 42

Olanzapine

Olanzapine is a low molecular weight drug used for the treatment of patients with schizophrenia.

A depot formulation precursor was formed by sequentially mixing 50 mg olanzapine, 360 mg PC and 100 mg of EtOH. 540 mg of GDO was added to the mixture resulting in the final depot formulation precursor.

Injecting the formulation precursor into excess water (syringe 23 G; 0.6 mm×30 mm) resulted in a monolithic liquid crystalline phase ($I_2$ structure).

Example 43

Acne Formulations with Clindamycin

Formulations were prepared as in previous examples by mixing the semisynthetic antibiotic clindamycin (free base or salt) with a mixture of GDO, PC, ethanol and PG in the following proportions (by weight).

| Formulation | Clindamycin HCl | PC | GDO | EtOH | PG |
|---|---|---|---|---|---|
| 1 | 1 | 30 | 54 | 10 | 5 |
| 2 | 2 | 29 | 54 | 10 | 5 |
| 3 | 1 | 34 | 50 | 10 | 5 |
| 4 | 2 | 33 | 50 | 10 | 5 |

| Formulation | Clindamycin base | PC | GDO | EtOH | PG |
|---|---|---|---|---|---|
| 5 | 1 | 30 | 54 | 10 | 5 |
| 6 | 2 | 29 | 54 | 10 | 5 |
| 7 | 1 | 33 | 54 | 2 | 10 |
| 8 | 2 | 32 | 54 | 2 | 10 |

The resulting preformulations are low viscosity liquids which, after application resistant to water, sweat, etc. The formulation are applied locally on the skin as a gel or by spraying and are bioadhesive with good film-forming properties.

Example 44

Further Examples of Viscosity in PC/GDO Mixtures on Addition of Co-Solvent

Mixtures of PC/GDO and co-solvent were prepared according to the methods of Example 1 and Example 3 in the proportions indicated in the table below. The samples were allowed to equilibrate for several days before viscosity measurements were performed using a Physica UDS 200 rheometer at 25° C.

| Sample | PC/GDO (wt/wt) | EtOH/ wt % | Glycerol/ wt % | H$_2$O/ wt % | Viscosity/ mPas |
|---|---|---|---|---|---|
| 1 | 50/50 | 3 | — | — | 1900 |
| 2 | 50/50 | 5 | — | — | 780 |
| 3 | 50/50 | 7 | — | — | 430 |
| 4 | 50/50 | 8 | — | — | 300 |
| 5 | 50/50 | 10 | — | — | 210 |
| 6 | 50/50 | 15 | — | — | 100 |
| 7 | 45/55 | 3 | — | — | 1350 |
| 8 | 45/55 | 5 | — | — | 540 |
| 9 | 45/55 | 7 | — | — | 320 |
| 10 | 45/55 | 8 | — | — | 250 |
| 11 | 45/55 | 10 | — | — | 150 |
| 12 | 45/55 | 15 | — | — | 85 |
| 13 | 40/60 | 3 | — | — | 740 |
| 14 | 40/60 | 5 | — | — | 400 |
| 15 | 40/60 | 7 | — | — | 240 |
| 16 | 40/60 | 8 | — | — | 200 |
| 17 | 40/60 | 10 | — | — | 130 |
| 18 | 40/60 | 15 | — | — | 57 |
| 19 | 40/60 | — | 10 | — | $8 * 10^6$ |
| 20 | 40/60 | — | — | 3 | $2.5 * 10^8$ |
| 21 | 40/60 | — | — | 5 | $4 * 10^7$ |

This example further illustrates the need for a solvent with viscosity lowering properties in order to obtain injectable formulations. The mixtures containing glycerol (sample 19) or water (samples 20 and 21) are too viscous to be injectable at solvent concentrations equivalent to the samples containing EtOH (compare with samples 13, 14 and 17).

Example 45

Occtreotide Formulation Compositions

Formulations were prepared as in Example 1 by mixing the peptide active octreotide with a mixture of GDO (at one of several purity levels) or tocopherol, PC, ethanol and optionally dioleoyl PG in the following proportions (by weight)

| Formulation | OCT | EtOH | PC | GDO1 | GDO2 | GDO3 | TP | DOPG |
|---|---|---|---|---|---|---|---|---|
| E | 2 | 10 | 35.2 | — | — | — | 52.8 | — |
| F | 2 | 10 | 35.2 | 52.8 | — | — | — | — |
| G | 2 | 10 | 35.2 | — | 52.8 | — | — | — |
| H | 2 | 10 | 26.4 | — | — | — | 61.6 | — |
| I | 1 | 10 | 35.6 | 53.4 | — | — | — | — |
| J | 2 | 5 | 37.2 | — | — | 55.8 | — | — |
| K | 3 | 5 | 36.8 | — | — | 55.2 | — | — |
| L | 6 | 5 | 35.6 | — | — | 53.5 | — | — |
| M | 3 | 5 | 35.8 | — | — | 55.2 | — | 1 |
| N | 3 | 5 | 33.8 | — | — | 55.2 | — | 3 |
| O | 3 | 5 | 30.8 | — | — | 55.2 | — | 6 |
| P | 3 | 5 | 46 | — | — | 46 | — | — |
| Q | 3 | 10 | 43.5 | — | — | 43.5 | — | — |
| R | 6 | 10 | 42 | — | — | 42 | — | — |
| S | 3 | 7 | 45 | — | — | 45 | — | — |
| T | 6 | 7 | 43.5 | — | — | 43.5 | — | — | where OCT is octreotide, EtOH is ethanol, PC is LIPOID S100 soybean phosphatidylcholine, GDO is glycerol dioleate, TP is α-tocopherol, DOPG is dioleoyl phosphatidylglycerol

| | GDO quality (according to AC) | | |
|---|---|---|---|
| | Monoglycerides | Diglycerides | Triglycerides |
| GDO1 | 10.9% | 87.5% | 1.4% |
| GDO2 | 4.2% | 92.1% | 3.5% |
| GDO3 | 0.5% | 95.3% | 4.0% |

Formulation P (for composition see above) was administered by s.c. injection in the rat at a level of 1 ml formulation per kg body weight, corresponding to 30 mg/kg of octreotide.

Octreotide plasma levels after administration were monitored for 5 days to examine any burst profile. It was observed that the highest plasma concentration was less than three fold greater than the average plasa concentration over the first 5 days.

The results of the study are shown in FIG. 6

Example 46

Sunscreen Formulations

Formulations were prepared as in Example 1 by mixing each of several UV absorbing/scattering agents with a mixture of GDO, PC, and ethanol in the following proportions (by weight)

| Formulation | PC | GDO | EtOH | Tioveil CM | Spectraveil FIN | Solaveil CT-100 | Tioveil 50 MOTG |
|---|---|---|---|---|---|---|---|
| 1 | 38 | 42 | 5 | — | — | — | 15 |
| 2 | 38 | 42 | 5 | — | — | 15 | — |
| 3 | 37 | 38 | 5 | 15 | 5 | — | — |

Where TIOVEIL CM (Uniqema) comprises Cyclomethicone (and) Titanium Dioxide (and) Dimethicone Copolyol (and) Aluminium Stearate (and) Alumina, SPECTRAVEIL FIN (Uniqema) comprises Zinc Oxide (and) C12-15 Alkyl Benzoate (and) Polyhydroxystearic Acid, SOLAVEIL CT-100 (Uniqema) comprises C12-15 Alkyl Benzoate (and) Titanium Dioxide (and) Polyhydroxystearic Acid (and) Aluminum Stearate (and) Alumina, and TIOVEIL 50 MOTG (Uniqema) comprises Titanium Dioxide (and) Caprylic/Capric Triglyceride(and) Mineral Oil (and) Polyhydroxystearic Acid (and) Aluminum Stearate (and) Alumina.

The resulting formulation precursors show low viscosity upon formulation and are readily applied by pump spray. Upon contact with body surfaces a resilient UV protective layer is formed.

Example 47

Chlorhexidine Periodontal Depots

Formulations were prepared as in Example 1 by mixing the antiinfective agent chlorhexidine digluconate with a mixture of GDO, PC, and ethanol in the following proportions (by weight)

TABLE

Chlorhexidine digluconate depot formulation compositions.

| Formulation | Chlorhexidine digluconate | PC | GDO | EtOH |
|---|---|---|---|---|
| A | 5 | 34 | 51 | 10 |
| B | 5 | 36 | 54 | 5 |
| C | 7 | 33 | 50 | 10 |
| D | 10 | 32 | 48 | 10 |
| E | 15 | 30 | 45 | 10 |

The chlorhexidine depot preformulations have low viscosity and are easily administered to the periodontal pocket. The compositions provide better distribution and spreading of the active substance throughout the periodontal pocket when compared to current products, such as Periochip®.

The depot formed after application gives protection against re-infection of the pocket. The depot also has excellent bioadhesive properties and sticks to mucosal, teeth and bone surfaces.

Release of chlorhexidine digluconate from 250 mg Formulation A (see above) in 0.9% aqueous NaCl (500 ml) was studied. The formulation was held in a cylindrical metal cup which was placed in a teflon holder at the bottom of a standard USP release bath. The contact area between the formulation and surrounding saline solution was 2.4 cm$^2$, and the solution was stirred by paddle at 100 rpm.

The release curve shown in FIG. 7 demonstrates the sustained and essentially uniform release of chlorhexidine from the formulation over a period of 24 hours.

The invention claimed is:

1. A non-liquid crystalline formulation precursor for the in vivo generation of a liquid crystalline lipid composition for the controlled release of at least one bioactive agent following parenteral administration, said formulation precursor comprising:
   i) a low-viscosity, non-liquid crystalline mixture having a viscosity of 1 to 1000 mPas at 20° C. and comprising:
      a) a minimum of 18 wt. % of a component consisting of at least one diacyl glycerol or at least one diacyl glycerol and at least one tocopherol;
      b) at least one phosphatidylcholine; and
      c) at least one biocompatible solvent comprising ethanol;
   ii) at least one bioactive agent dissolved or dispersed in the low viscosity mixture;
   wherein the formulation precursor forms at least one liquid crystalline phase structure in vivo upon contact with an aqueous fluid.

2. A non-liquid crystalline formulation precursor for the in vivo generation of a liquid crystalline lipid composition for the controlled release of at least one bioactive agent following parenteral administration, said formulation comprising:
   i) a low-viscosity, non-liquid crystalline mixture having a viscosity of 1 to 1000 mPas at 20° C. and comprising:
      a) a minimum of 18 wt. % of a component consisting of at least one tocopherol and at least one diacyl glycerol;
      b) at least one phosphatidylcholine; and
      c) at least one biocompatible, oxygen containing, low viscosity organic solvent;
   ii) at least one bioactive agent dissolved or dispersed in the low viscosity mixture;
   wherein the formulation precursor forms at least one liquid crystalline phase structure in vivo upon contact with an aqueous fluid.

3. The formulation precursor as claimed in claim 1 wherein component a) consists essentially of diacyl glycerols.

4. The formulation precursor as claimed in claim 3 wherein said diacyl glycerols comprise glycerol dioleate.

5. The formulation precursor as claimed in claim 1 wherein component a) consists essentially of a mixture of glycerol dioleate (GDO) and tocopherol.

6. The formulation precursor as claimed in claim 1 having a molecular solution, $L_2$ and/or $L_3$ phase structure.

7. The formulation precursor as claimed in claim 1 having a ratio of a) to b) of between 95:5 and 5:95 by weight.

8. The formulation precursor as claimed in claim 1 having 0.5 to 50% component c) by weight of components a)+b)+c).

9. The formulation precursor as claimed in claim 1 additionally comprising up to 10% by weight of a)+b) of a charged amphiphile.

10. The formulation precursor as claimed in claim 1 wherein said active agent is selected from drugs, antigens, nutrients, cosmetics, fragrances, flavourings, diagnostic agents, vitamins, dietary supplements and mixtures thereof.

11. The formulation precursor as claimed in claim 10 wherein said drug is selected from hydrophilic small molecule drugs, lipophilic small molecule drugs, amphiphilic small molecule drugs, peptides, proteins, oligonucleotides and mixtures thereof.

12. The formulation precursor as claimed in claim 10 wherein said drug is selected from somatostatin related peptides, interferons, glucagon-like peptides 1 and 2, GnRH agonists, GnRH antagonists, bisphosphonates, chlorhexidine and mixtures thereof.

13. The formulation precursor as claimed in claim 1 which is administrable by injection.

14. An injectable formulation precursor as claimed in claim 1 which forms a depot providing continuous release of active agent for at least two weeks, wherein said active agent comprises at least one selected from
   i. octreotide
   ii. human growth hormone
   iii. interferon alpha
   iv. leuprolide.

15. An injectable formulation precursor as claimed in claim 1 which forms a depot providing continuous release of active agent for at least two weeks, wherein said active agent comprises at least one selected from
   i. risperidone
   ii. olanzapine
   iii. testosterone undecanoate.

16. A method of delivery of a bioactive agent to a human or non-human animal (preferably mammalian) body, this method comprising administering the formulation precursor as claimed in claim 1 whereby to form at least one liquid crystalline phase structure upon contact with an aqueous fluid in vivo following administration.

17. The method as claimed in claim 16 wherein said formulation precursor is administered by a method selected from subcutaneous injection, intramuscular injection, intra-cavity injection through tissue, intra-cavity injection into an open cavity without tissue penetration.

18. A method for the preparation of a liquid crystalline composition comprising exposing the formulation precursor as claimed in claim 1 to an aqueous fluid in vivo.

19. A process for the formation of a formulation precursor for the administration of a bioactive agent to a mammalian subject, said process comprising:
   i) forming a non-liquid crystalline, low viscosity mixture having a viscosity of 1 to 1000 mPas at 20° C. and comprising:
      a) a minimum of 18 wt. % of at least one neutral diacyl glycerol or at least one neutral diacyl glycerol and at least one tocopherol;
      b) at least one phosphatidylcholine;
      c) at least one biocompatible solvent having a viscosity of no more than 15 mPas at 20° C. comprising ethanol; and
   ii) dissolving or dispersing at least one bioactive agent in the low viscosity mixture, or in at least one of components a, b or c prior to forming the low viscosity mixture.

20. A process for the formation of a formulation precursor for the administration of a bioactive agent to a mammalian subject, said process comprising:

i) forming a non-liquid crystalline, low viscosity mixture having a viscosity of 1 to 1000 mPas at 20° C. and comprising:

a) a minimum of 18 wt. % of at least one tocopherol and least one diacyl glycerol;

b) at least one phosphatidylcholine;

c) at least one biocompatible, oxygen containing, low viscosity organic solvent; and ii) dissolving or dispersing at least one bioactive agent in the low viscosity mixture, or in at least one of components a, b or c prior to forming the low viscosity mixture.

21. A process as claimed in claim 19 wherein said formulation precursor is the formulation precursor as claimed in claim 1.

22. A method of treatment or prophylaxis of a human or non human animal subject comprising parenteral administration of the formulation precursor as claimed in claim 1.

23. The method of claim 22 for the treatment of a condition selected from bacterial infection, fungal infection, skin soreness, eye conditions, genital soreness, infections and conditions for the finger and/or toe nails, travel sickness, addiction including nicotine addiction, periodontal infection, conjunctivitis, glaucoma and hormone deficiency or imbalance.

24. The method of claim 22 for prophylaxis against at least one condition selected from infection during surgery, infection during implantation, sunburn, infection at the site of burns, cuts or abrasions, oral infections, genital infections and infections resulting from activities resulting in exposure to infective agents.